(12) United States Patent
Brambilla et al.

(10) Patent No.: US 11,471,502 B2
(45) Date of Patent: Oct. 18, 2022

(54) NEUROPROTECTIVE PEPTIDE

(71) Applicant: UNIVERSITY COLLEGE CARDIFF CONSULTANTS LTD, South Glamorgan (GB)

(72) Inventors: Riccardo Brambilla, South Glamorgan (GB); Stefania Fasano, Milan (IT); Marzia Indrigo, Milan (IT); Alessandro Papale, Milan (IT)

(73) Assignee: University College Cardiff Consultants Ltd, South Glamorgan (GB)

( * ) Notice: Subject to any disclaimer, the term of this patent is extended or adjusted under 35 U.S.C. 154(b) by 17 days.

(21) Appl. No.: 16/765,962

(22) PCT Filed: Nov. 23, 2018

(86) PCT No.: PCT/GB2018/053384
§ 371 (c)(1),
(2) Date: May 21, 2020

(87) PCT Pub. No.: WO2019/102201
PCT Pub. Date: May 31, 2019

(65) Prior Publication Data
US 2020/0360460 A1 Nov. 19, 2020

(30) Foreign Application Priority Data

Nov. 24, 2017 (GB) .................................. 1719520

(51) Int. Cl.

| | | |
|---|---|---|
| A61K 38/45 | (2006.01) | |
| A61K 45/06 | (2006.01) | |
| A61K 38/00 | (2006.01) | |
| A61P 25/16 | (2006.01) | |
| A61P 25/28 | (2006.01) | |
| C07K 14/00 | (2006.01) | |
| C12N 9/12 | (2006.01) | |

(52) U.S. Cl.
CPC ............ *A61K 38/005* (2013.01); *A61P 25/16* (2018.01); *A61P 25/28* (2018.01); *A61K 45/06* (2013.01)

(58) Field of Classification Search
CPC ...... A61K 38/005; A61K 38/45; A61K 45/06; A61K 38/00; A61P 25/16; A61P 25/28; C07K 2319/10; C07K 14/00; C12N 9/12; C12Y 207/11024
See application file for complete search history.

(56) References Cited

U.S. PATENT DOCUMENTS

| | | | | |
|---|---|---|---|---|
| 6,849,716 | B1 * | 2/2005 | Su ........................ | C12N 9/1205 530/350 |
| 7,033,790 | B2 * | 4/2006 | Patturajan .............. | C07K 14/47 435/320.1 |
| 2004/0023292 | A1 * | 2/2004 | McSwiggen ........... | G01N 33/68 435/7.1 |
| 2017/0227551 | A1 * | 8/2017 | Beskrovnaya .......... | A61P 13/12 |

FOREIGN PATENT DOCUMENTS

| | | |
|---|---|---|
| JP | H09216900 A | 8/1997 |
| WO | WO03/057709 A2 | 7/2003 |
| WO | WO2006/087242 A2 | 8/2006 |

OTHER PUBLICATIONS

Yampolsky et al., "The Exchangeability of Amino Acids in Proteins," Genetics, 2005, 170: 1459-1472. (Year: 2005).*
Copolovici et al., "Cell-Penetrating Peptides: Design, Synthesis, and Applications," AcNANO, 2014, 8(3): 1972-1994. (Year: 2014).*
Fears, Kyle, "Exploration and Manipulation of Cellular Pathways for Treatment of Neurodegeneration," Doctoral Thesis, Cardiff University, Jan. 2019, pp. 1-254. (Year: 2019).*
International Search Report and Written Opinion for PCT/GB2018/053384 dated Jan. 25, 2019.
Great Britain Intellectual Property Office Search Report dated Aug. 16, 2018.
WO2006/087242—English machine translation.
JPH09216900A—English machine translation.
Horiuchi, K.Y., et al., Competitive Inhibition of MAP Kinase Activation by a Peptide Representing the ac Helix of ERK; Biochemistry,vol. 37, 1998; pp. 8879-8885.
Boulton, T.G., et al., Identification of multiple extracellular signal-regulated kinases (ERKs) with antipeptide antibodies, Cell Regulation, vol. 2, pp. 357-371, May 1991.
Marchi, M., et al., The N-Terminal Domain of ERK1 Accounts for the Functional Differences with ERK2; PLoS ONE, vol. 3, Dec. 2008; pp. 1-13.
Vantaggiato, C., et al., ERK1 and ERK2 mitogen-activated protein kinases affect Ras-dependent cell signaling differentially; Journal of Biology 2006, vol. 5, Article 14.

* cited by examiner

*Primary Examiner* — Julie Ha
(74) *Attorney, Agent, or Firm* — Patrick M. Torre; Stites & Harbison, PLLC

(57) ABSTRACT

Inhibitors of MAPK3 (ERK1 MAP kinase), in particular polypeptides having the ability to stimulate the global ERK signalling pathway in the brain and their use as neuroprotective and/or cognitive enhancing agents, are disclosed. Related polynucleotides, vectors, host cells and pharmaceutical compositions able to inhibit MAPK3, causing the stimulation of the global ERK signalling pathway, are also disclosed. Additionally, use of the afore inhibitors or stimulators in the treatment of neurodegenerative or neuropsychiatric disorders and cognitive impairment is also disclosed.

Figure 1A:
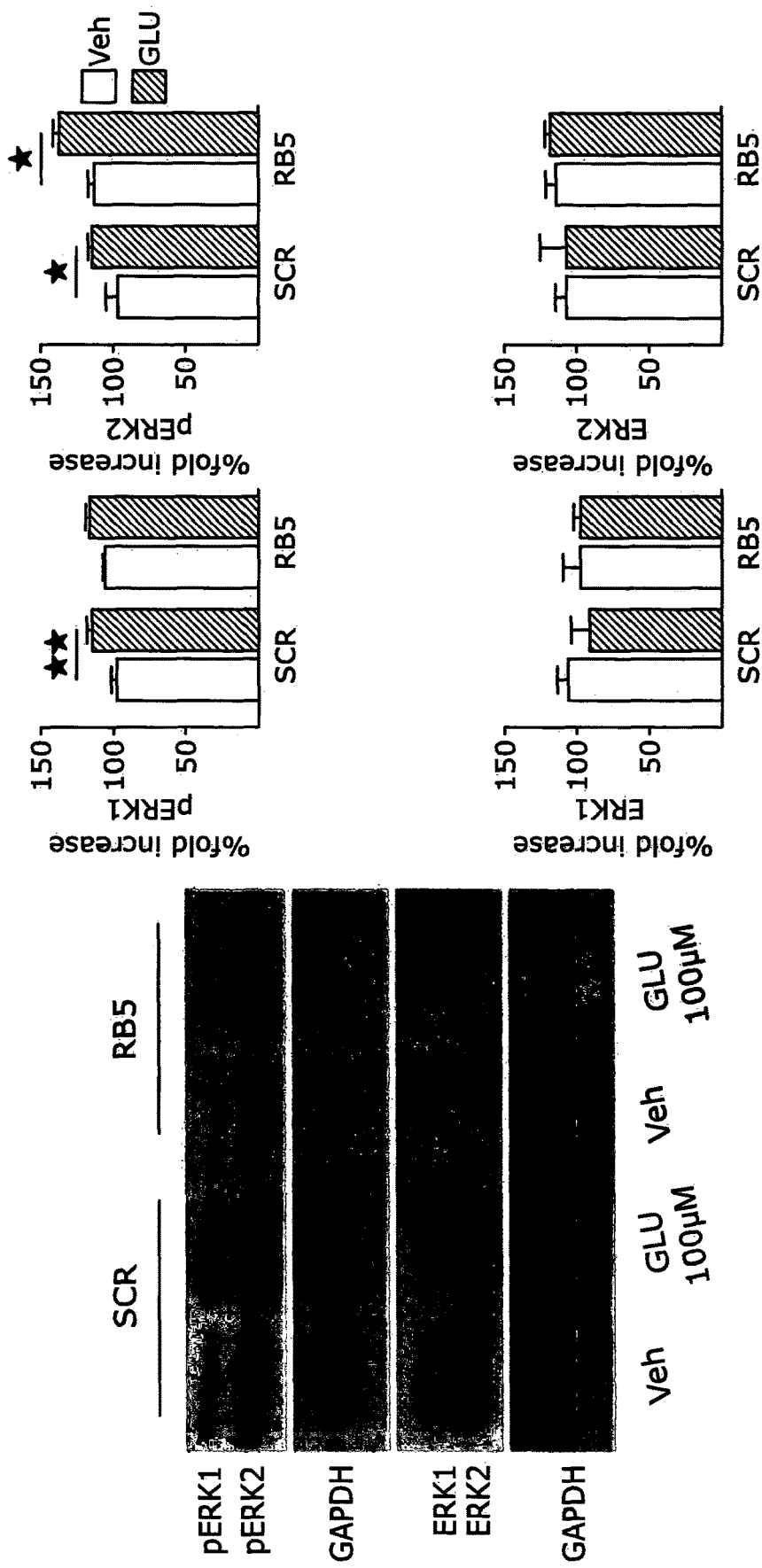

7 Claims, 22 Drawing Sheets
Specification includes a Sequence Listing.

e)

NEUROPROTECTIVE PEPTIDE

This application is the national stage of international patent application no. PCT/GB2018/053384 filed on Nov. 23, 2018, which in turn claims priority from Great Britain Patent Application No. 1719520.7 filed on Nov. 24, 2017, the disclosures of which are incorporated herein by reference in their entirety.

REFERENCE TO SEQUENCE LISTING SUBMITTED ELECTRONICALLY

A sequence listing electronically submitted with the present application as an ASCII text file named 1776-064SequenceListing_ST25.txt, created on 5-19-2020 and having a size of 6000 bytes, is incorporated herein by reference in its entirety.

TECHNICAL FIELD

The invention relates to inhibitors of MAPK3 (ERK1 MAP kinase), in particular to polypeptides having the ability to stimulate the global ERK signalling pathway in the brain and their use as neuroprotective and/or cognitive enhancing agents. The invention also concerns related polynucleotides, vectors, host cells and pharmaceutical compositions able to inhibit MAPK3, causing the stimulation of the global ERK signalling pathway. Additionally, use of the afore inhibitors or stimulators in the treatment of neurodegenerative or neuropsychiatric disorders and cognitive impairment is also disclosed.

BACKGROUND

The Extracellular signal Regulated Kinase (ERK) cascade is a signalling pathway involved in a variety of cellular processes, from cell proliferation and survival, to differentiation and behavioural plasticity. In the brain, this cascade provides a link between ionotropic, metabotropic and neurotrophin receptors to cytosolic (regulation of ion channels and of protein translation) and nuclear events, leading to gene transcription, de novo protein synthesis and changes either in synaptic remodelling and plasticity, memory formation, or neuronal survival, depending on the context. Once activated by neurotransmitter receptors through GTP/GDP exchange factors, the small GTPases belonging to the Ras class (p21 H-, K- and N-Ras gene products) stimulate sequentially the cascade of protein kinases consisting of serine/threonine kinases of the Raf subfamily (mainly c-Raf and B-Raf, the MAPK Kinase Kinase tier), the threonine/tyrosine dual specificity kinases MEK1/2 (MAPK Kinase) and finally ERK1/2 proteins (the MAPK component). More specifically, activation of MEK1/2 leads to a selective interaction with ERK proteins through specific docking domains which result in phosphorylation of the conserved recognition motif of threonine and tyrosine (TEY domain), within the activation loop of ERK1/2.

ERK1 and ERK2, also known as MAPK3 and MAPK1, respectively, are homologous isoforms produced by two genes, MAPK3 and MAPK1. ERK1 and ERK 2 share nearly 85% amino acid identity, but exhibiting greater identity in the core regions. Both isoforms are expressed in essentially all cells, although ERK2 is the predominant isoform in brain and hematopoietic cells. Once activated, ERK1 and ERK2, the two major MAPKs in the brain, are able to translocate into the nucleus. There, they can activate either directly or indirectly (via the kinases of the RSK families), transcription factors such as the CREB-like class of transcriptional regulators, or regulate chromatin remodelling (via the kinases of the MSK family). The ability of ERK to regulate gene expression and chromatin organization is believed to be a crucial step not only in the processes of neural adaptation underlying normal cognitive processes but also in the onset of several neuropsychiatric disorders.

A crucial permissive role for ERK dependent signalling in memory formation and consolidation is apparently well established. However, early findings have essentially been based on the use of chemical inhibitors of MEK kinases, indirectly affecting ERK1 and ERK2 in the brain, leading to memory deficits in a variety of learning tasks. Unfortunately, the possibility that a general activation of ERK mediated gene expression and chromatin remodelling in the adult brain can effectively result in cognitive enhancement remains unproven, thus precluding the development of effective treatments for memory and neurodegenerative disorders. At the same time, conflicting evidence is available supporting either a pro-survival activity of ERK signalling in the brain or a pro-apoptotic role.

Cognitive decline is a major feature of most neurodegenerative disorders. Unfortunately, while treatments aimed at improving memory functions in patients do not necessarily delay the degenerative process, a neuroprotective approach may not be sufficient to preserve or restore behavioural plasticity observed in healthy individuals.

There is still a large unmet medical need with substantial commercial potential for an effective product for the treatment of neurodegenerative disorders and their associated irreversible cognitive decline. Example of such disorders are Parkinson's Disease, Alzheimer's Disease and Huntington's Disease in which a progressive loss of neuronal cell population leads to impaired brain functions, learning and memory deficits and, ultimately, death.

In the present invention it was surprisingly found that peptides derived from the N-terminal domain of ERK1 can achieve selective activation of nuclear ERK signalling, through the inhibition of MAPK3 protein kinase in the cytoplasm. The peptides of the invention can specifically stimulate nuclear translocation of ERK and thus stimulate ERK-mediated gene transcription and chromatin remodelling in the brain. Administration of these peptides promotes ERK dependent nuclear signalling in response to glutamate; decreases neuronal death, enhances memory consolidation and improves memory acquisition and memory formation. Thus, through administration of these peptides we have shown that one can i) improve memory in healthy individuals (cognitive enhancement), ii) prevent neurodegeneration, such as that observed in Parkinson's, Alzheimer's and Huntington's Diseases and iii) retard memory decline, for example, as observed in forms of dementia and Alzheimer's Disease. It is therefore proposed that the peptides of the invention display positive effects on both neuronal cell survival and cognition and represent a therapy for a number of major brain disorders, currently without effective treatment, both improving cognitive deficits and blocking neurodegeneration. Moreover, given the peptides of the invention improve cognition in the absence of neurodegeneration, they are suitable for cognitive enhancement in healthy individuals.

SUMMARY

According to a first aspect of the invention there is provided a neuroprotective peptide for inhibiting Mitogen-activated protein kinase 3 (MAPK3) protein kinase signalling comprising an amino acid sequence:
  i) QGGGGGEPRRTEGVGPGVPGEVEMVKGQPFDV (SEQ ID NO:1) hereafter named RB5; or
  ii) a sequence sharing at least 75% identity with peptide i).

MAPK3 refers to Mitogen-activated protein kinase 3 (MAPK3), an enzyme that in humans is encoded by the MAPK3 gene. The protein encoded by this gene is a member of the MAP kinase family. MAP kinases, also known as extracellular signal-regulated kinases (ERKs), act in a signalling cascade that regulates various cellular processes such as proliferation, differentiation, and cell cycle progression in response to a variety of extracellular signals. This kinase is activated by upstream kinases, resulting in its translocation to the nucleus where it phosphorylates nuclear targets. Spliced transcript variants encoding different protein isoforms have been described. MAPK3 has several synonyms, namely ERK-1; ERK1; ERT2; HS44KDAP; HUMKER1A; P44ERK1; P44MAPK; PRKM3; p44-ERK1; p44-MAPK.

The peptide of the present invention causes the stimulation of global ERK signalling in the nucleus. By "global ERK signalling" it is meant the enhanced activity of MAPK1/ERK2, the major ERK isoforms that govern the signalling mechanisms associated with this pathway.

The skilled person will appreciate that homologues, orthologues or functional derivatives of the peptide will also find use in the context of the present invention. Thus, for instance peptides which include one or more additions, deletions, substitutions or the like are encompassed by the present invention. In addition, it may be possible to replace one amino acid with another of similar "type". For instance, replacing one hydrophobic amino acid with another one can be achieved by using a program such as the CLUSTAL program to compare amino acid sequences. This program compares amino acid sequences and finds the optimal alignment by inserting spaces in either sequence as appropriate. It is possible to calculate amino acid identity or similarity (identity means conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

Allelic variants, refer to variants of peptides in the same species, orthologous peptides of the invention refer to variants in different species. Examples of orthologous are mouse MAPK3 (NP_036082.1), *Rattus norvegicus* MAPK3 (NP_059043.1), *Canis lupus familiaris* MAPK3 (NP_001238964.1) *Danio rerio* MAPK3 (NP_958915.1) *Salmo salar* MAPK3 (NP_001167267.1), *Pongo abelii* MAPK3 isoform 1 (XP_002826343.1), *Papio anubis* MAPK3 isoform 1 (XP_003916792.1), *Tursiops truncatus* MAPK3 isoform 1 (XP_004316634.1), *Callithrix jacchus* MAPK3 (XP_002807461.1), *Bos taurus* MAPK3 isoform X1 (XP_005224976.1), *Otolemur garnettii* MAPK3 (XP_003795827.1), *Odobenus rosmarus divergens* MAPK3 isoform 1 (XP_004397229.1), *Vicugna pacos* MAPK3 isoform X1 (XP_006201318.1), *Cavia porcellus* MAPK3 (XP_003478275.1), *Heterocephalus glaber* MAPK3 (XP_004856331.1), *Dasypus novemcinctus* MAPK3-like (XP_004461533.1), *Leptonychotes weddellii* MAPK3 (XP_006750264.1), *Equus caballus* MAPK3 (XP_001915560.1), *Trichechus manatus latirostris* MAPK3 isoform 1 (XP_004386681.1), *Ceratotherium simum simum* MAPK3 (XP_004439579.1), *Microtus ochrogaster* MAPK3 (XP_005351990.1), *Mustela putorius furo* MAPK3, XP_004774094.1, XP_004816989.1), *Chinchilla lanigera* MAPK3
  (XP_005405403.1), *Pan troglodytes* MAPK3 (XP_510921.3), *Octodon degus* MAPK3 isoform X1 (XP_004622998.1), *Monodelphis domestica* MAPK3 (XP_001364363.1), *Pantholops hodgsonii* MAPK3 (XP_005963252.1), *Pongo abelii* MAPK3 isoform 2 (XP_003778644.1), *Papio anubis* MAPK3 isoform 2 (XP_003916793.1), *Tursiops truncatus* MAPK3 isoform 2 (XP_004316635.1), *Vicugna pacos* MAPK3 isoform X2 (XP_006201319.1), *Xiphophorus maculatus* MAPK1-like
  (XP_005813410.1), *Takifugu rubripes* MAPK1-like (XP_003975118.1), *Trichechus manatus latirostris* MAPK3 isoform 2 (XP_004386682.1), *Odobenus rosmarus divergens* MAPK3 isoform 2 (XP_004397230.1), *Latimeria chalumnae* MAPK3-like (XP_006005975.1).

The term "homologue/homologous" as used herein refers to amino acid sequences which have a sequence with at least 75% homology or similarity or identity to/with the amino acid sequence of QGGGGGEPRRTEGVGPGVPGEVEMVKGQPFDV (SEQ ID NO:1) and which retain the biological activity or MAPK3 inhibitory function of QGGGGGEPRRTEGVGPGVPGEVEMVKGQPFDV (SEQ ID NO:1). It is preferred that peptides have at least 75% identity with the peptide sequence of i), and in increasing order of preference, at least 76%, 77%, 78%, 79%, 80%, 81%, 82%, 83%, 84%, 85%, 86%, 87%, 88%, 89%, 90%, 91%, 92%, 93%, 94% 95%, 96%, 97%, 98% or 99% identity with QGGGGGEPRRTEGVGPGVPGEVEMVKGQPFDV (SEQ ID NO:1).

In yet a further preferred embodiment of the first aspect of the invention, said peptide comprises, or consists of, the sequence QGGGGGEPRRTEGVGPGVPGEVEMVKGQPFDV (SEQ ID NO:1).

In a further preferred embodiment of the invention, said neuroprotective peptide is covalently or non-covalently attached to or associated with a peptide carrier for the purpose of transporting said selected peptide across a membrane, typically, but not exclusively, a biological membrane. In this arrangement, advantageously, the peptide carrier permits passage through the brain blood barrier and/or through plasma membranes of neuronal cells. Thus, the peptide can be delivered into cells, particularly, into cells of the brain.

As will be appreciated by those skilled in the art, said biological membrane may be the membrane surrounding a cell. This may include, but is not limited to, membranes such as the simple plasma membrane or more specialized membrane structures including apical, basolateral, presynaptic and postsynaptic membranes, membranes of flagella, cilia, microvillus, filopodia and lamellipodia, the sarcolemma of muscle cells, as well as specialized myelin and dendritic spine membranes of neurons. Additionally, or alternatively, said membrane may be that of an organelle located within the cell, permitting delivery of the peptide to a specific internal cellular compartment. This may include organelles such as, but not limited to, endosome; smooth and rough endoplasmic reticulum; sarcoplasmic reticulum; Golgi apparatus; lysosome; mitochondrion (inner and outer membranes); nucleus (inner and outer membranes); peroxisome; vacuole; cytoplasmic granules; cell vesicles (phagosome, autophagosome, clathrin-coated vesicles, COPI-coated and COPII-coated vesicles) and secretory vesicles.

Additionally, said biological membrane includes reference to any membrane of Eukaryotic or Prokaryotic origin.

Ideally, said neuroprotective peptide is attached to said peptide carrier at either its amino or carboxy terminal.

In yet a further preferred embodiment of the first aspect of the invention, said selected neuroprotective peptide is attached immediately next to or to the amino acid residues of said peptide carrier. Alternatively, said selected neuroprotective peptide is located distally from the amino acid residues of said peptide carrier due to the presence of at least one further amino acid residue or a spacer preferably represented by a number of amino acid residues selected from the group comprising or consisting of 2, 3, 4, 5, 6, 7, 8, 9, 10, 11, 12, 13, 14, 15, 16, 17, 18, 19, and 20 amino acid residues. As will be appreciated by those skilled in the art, this may improve permeability of the selected neuroprotective peptide, however, other spacers that can perform this function, ideally but not exclusively to equal effect, may be used in the working of the invention.

More preferably, said peptide carrier is a cell penetrating peptide (CPP). Reference herein to a CPP refers to a short peptide sequence, typically less than 30 amino acids, that possesses the ability to translocate the plasma membrane when co-joined with at least one selected molecule. Thus, use of a CPP with a peptide of the invention facilitates the delivery of said peptide into a cell or an organelle. CPPs, typically, are used to overcome the impermeability of membranes. Hundreds of different CPP sequences have now been described in the art and all have a universal capacity to cross or breach biological membranes and enter cells, either alone or when associated with cargo. Suitable CPPs are known in the art such as, but not limited to, HIV-TAT, Penetratin™, short sequences of amino acids with a high density of basic (+) charge (commonly a string of Lysine or Arginine residues e.g. octarginine), or the Antennapedia peptide. Most ideally, said peptide carrier is a CPP selected from the group comprising:

```
                                        (SEQ ID NO: 2)
GRKKRRQRRR;

(SEQ ID NO: 3)
RQIKIWFQNRRMKWKK;

(SEQ ID NO: 4)
RRRRRRR;

(SEQ ID NO: 5)
XRRRRRRRX;

(SEQ ID NO: 6)
XRRRXRRRR;

(SEQ ID NO: 7)
RRRXRRRRX;

(SEQ ID NO: 8)
RRRRRRRXX;

(SEQ ID NO: 9)
XXRRRRRRR;

(SEQ ID NO: 10)
RRRRRRRRRR;

(SEQ ID NO: 11)
XRRRRRXRRRRRR;

(SEQ ID NO: 12)
RRRRRXRRRRRRX;
```

```
                                        (SEQ ID NO: 13)
GAYDLRRRERQSRLRRRERQSR;

(SEQ ID NO: 14)
SRRARRSPRHLGSG;

(SEQ ID NO: 15)
LRRERQSRLRRERQSR;

(SEQ ID NO: 16)
VKRGLKLRHVRPRVTRMDV
and (SEQ ID NO: 17)
RKKRRRESRKKRRRES.
```

Most preferably, said neuroprotective peptide comprises, or consists, of the sequence GRKKRRQRRRPPQGGGGGEPRRTEGVGPGVP-GEVEMVKGQPFDV (SEQ ID NO:18) hereafter named CPP-RB5.

According to yet a second aspect of the invention there is provided a nucleic acid molecule encoding the peptide according to the invention. Preferably, said nucleic acid refers to refers to RNA or DNA, most preferably to DNA. Said DNA may be double-stranded or single-stranded.

According to a third aspect of the invention there is provided a vector comprising said nucleic acid molecule.

As used herein, the term "vector" refers to an expression vector, and may be for example in the form of a plasmid, a viral particle, a phage, lipid based vehicle and cell based vehicles. Examples of such delivery vehicles include: biodegradable polymer microspheres, lipid based formulations such as liposome carriers, coating the construct onto colloidal gold particles, lipopolysaccharides, polypeptides, polysaccharides, pegylation of viral vehicles etc. Further, such vectors may also include: adenoviruses, retroviruses, lentiviruses, adeno-associated viruses, herpesviruses, vaccinia viruses, foamy viruses, cytomegaloviruses, Semliki forest virus, poxviruses, pseudorabies, RNA virus vector and DNA virus vector. Such viral vectors are well known in the art. Further the invention includes bacterial plasmids, phage DNA, baculovirus, yeast plasmids, vectors derived from combinations of plasmids and phage DNA. Large numbers of suitable vectors are known to those of skill in the art and are commercially available. The following vectors are provided by way of example. Bacterial: pQE70, pQE60, pQE-9 (QIAGEN), pbs, pDIO, phagescript, psiX174, pbluescript SK, pbsks, pNH8A, pNHI[beta]a, pNH18A, pNH46A (STRATAGENE), ptrc99a, pKK223-3, pKK233-3, pDR540, pRIT5 (PHARMACIA). Eukaryotic: pWLNEO, pSV2CAT, pOG44, pXTI, pSG (STRATAGENE), pSVK3, pBPV, pMSG, pSVL (PHARMACIA). However, any other vector may be used as long as it is replicable and viable in the host. The polynucleotide sequence, preferably the DNA sequence in the vector is operatively linked to an appropriate expression control sequence(s) (promoter) to direct mRNA synthesis. As representative examples of such promoters, one can mention prokaryotic or eukaryotic promoters such as CMV immediate early, HSV thymidine kinase, early and late SV40, LTRs from retrovirus, and mouse metallothionein-I. The expression vector also contains a ribosome-binding site for translation initiation and a transcription vector. The vector may also include appropriate sequences for amplifying expression.

In addition, the vectors preferably contain one or more selectable marker genes to provide a phenotypic trait for selection of transformed host cells such as dihydrofolate reductase or neomycin resistance for eukaryotic cell culture, or such as tetracycline or ampicillin resistance in *E. coli*.

According to a fourth aspect of the invention there is provided a host cell transformed or transfected with said vector.

As used herein, the term "host cell" relates to host cells, which have been transduced, transformed or transfected with the polynucleotide or with the vector described previously. As representative examples of appropriate host cells, one can mention bacterial cells, such as *E. coli, Streptomyces, Salmonella typhimurium*, fungal cells such as yeast, insect cells such as Sf9, animal cells such as CHO or COS, plant cells, etc. The selection of an appropriate host is deemed to be within the scope of those skilled in the art from the teachings herein. Preferably, said host cell is an animal cell, and most preferably a human cell.

According to a further aspect of the invention there is provided a neuroprotective peptide as defined herein for use as a medicament.

According to yet a further aspect of the invention there is provided a neuroprotective peptide as defined herein for use in the treatment or prevention of a neurodegenerative disorder.

According to yet a further aspect of the invention there is provided a neuroprotective peptide as defined herein for use in the manufacture of a medicament to treat or prevent a neurodegenerative disorder.

According to a further aspect of the invention there is provided a pharmaceutical composition comprising the neuroprotective peptide and a suitable carrier, emollient, diluent or adjuvant.

According to a yet further aspect of the invention there is provided a combination therapeutic for use in the treatment or prevention of a neurodegenerative disorder comprising a neuroprotective peptide and/or pharmaceutical composition as herein described and at least one other therapeutic for treating or preventing a condition of the brain.

Said additional therapeutic may include:

a) cognitive enhancers (nootropics): methylphenidate, racetams, isoflavones, vitamins (B, C, D, E), choline, amphetamines, xanthines, adrenergics, cholinergics, serotonigergic, dopaminergics, eugeroics (adrafinil, armodafinil, modafinil), GABA blockers, AMPAkines, PDE4 inhibitors and others;

b) neuroprotective agents: glutamate antagonists, 17β-Estradiol, ginsenoside Rd, progesterone, statins, antioxidants, nicotine, caffeine, caspase inhibitors, neurotrophic factors, other antiapoptotic agents; or c) analgesics.

According to an even further aspect of the invention, there is provided a method for treating or preventing a neurodegenerative disorder comprising administering an effective amount of the neuroprotective peptide and/or nucleic acid molecule and/or vector and/or pharmaceutical composition as defined herein to a patient in need thereof.

Reference herein to a neurodegenerative disorder includes, but is not limited to, Alzheimer's Disease (AD) and other dementia's; Huntington's Disease (HD); Parkinson's Disease (PD); degenerative nerve diseases; encephalitis; epilepsy; genetic brain disorders; head and brain malformations; hydrocephalus; stroke; multiple sclerosis; amyotrophic lateral sclerosis (ALS or Lou Gehrig's Disease); Fronto-temporal Dementia (FTP); Progressive Supranuclear Palsy (PSP); Essential Tremor (ET); Multiple System Atrophy (MSA); Corticobasal Degeneration (CBD); Cerebral Ischemia; Lysosomal Storage Diseases (LSD). Preferably, the neurodegenerative disorder is selected from the group comprising: Alzheimer's Disease (AD) and other dementia's; and Huntington's Disease (HD); Parkinson's Disease (PD).

Reference herein to an "effective amount" of the peptide or a composition comprising same is one that is sufficient to achieve a desired biological effect, in this case neuroprotection and/or cognitive enhancement. It is understood that the effective dosage will be dependent upon the age, sex, health, and weight of the recipient, kind of concurrent treatment, if any, frequency of treatment, and the nature of the effect desired. Typically, the effective amount is determined by those administering the treatment.

According to a further aspect of the invention there is provided a neuroprotective peptide as defined herein for use in the treatment or prevention of a neuropsychiatric disorder.

According to a further aspect of the invention there is provided a neuroprotective peptide as defined herein for use in the manufacture of a medicament to treat or prevent a neuropsychiatric disorder.

According to a yet further aspect of the invention there is provided a combination therapeutic for use in the treatment or prevention of a neuropsychiatric disorder comprising a neuroprotective peptide and/or pharmaceutical composition as herein described and at least one other therapeutic for treating a condition of the brain.

According to a further aspect of the invention, there is provided a method for treating or preventing a neuropsychiatric disorder comprising administering an effective amount of the neuroprotective peptide and/or nucleic acid molecule and/or vector and/or pharmaceutical composition as defined herein to a patient to be treated.

Reference herein to a neuropsychiatric disorder includes, but is not limited to autism spectrum disorder (ASD), intellectual disabilities (ID), schizophrenia, psychosis, mania (also known as hypomania and bipolar disorder when it alternates with depression), major depression, anxiety, post-traumatic stress disorder, obsessive-compulsive disorder.

According to a yet further aspect of the invention there is provided a neuroprotective peptide as defined herein for use as a cognitive enhancing agent.

Those skilled in the art will appreciate that in this aspect of the invention said neuroprotective peptide is used, not to prevent or treat a disease, but to improve, ideally intermittently but possibly chronically, cognitive ability. Thus in this context cognitive ability or cognitive enhancement is not regarded as a disease. Thus the neuroprotective peptide may be formulated as a dietary supplement or as a part of a food product, such as but not exclusively, a health food product.

According to a yet further aspect of the invention there is provided a combination therapeutic for use in the enhancement of cognitive ability comprising a peptide and/or pharmaceutical composition as herein described and at least one other cognitive enhancing agent and/or analgesic.

According to a further aspect of the invention, there is provided a method for enhancing cognitive ability comprising administering an effective amount of the neuroprotective peptide and/or nucleic acid molecule and/or vector and/or pharmaceutical composition as defined herein to an individual needing or desiring said improved cognitive ability.

Reference herein to cognitive ability includes, but is not limited to, brain-based skills one needs to carry out any task from the simplest to the most complex such as remembering, paying attention, listening, seeing, concentrating, focusing, reasoning, deliberating, analyzing, sensing, understanding.

They have more to do with the mechanisms of how we learn, remember, problem-solve, and pay attention, rather than with any actual knowledge.

Compounds for use in medicine will generally be provided in a pharmaceutical or veterinary composition and therefore according to a yet further aspect of the invention there is provided a pharmaceutical composition comprising a peptide as defined herein and a pharmaceutically acceptable carrier, adjuvant, diluent or excipient.

Suitable pharmaceutical excipients are well known to those of skill in the art. Pharmaceutical compositions may be formulated for administration by any suitable route, for example oral, buccal, nasal or bronchial (inhaled), transdermal or parenteral and may be prepared by any methods well known in the art of pharmacy.

The composition may be prepared by bringing into association the above defined peptide with the carrier. In general, the formulations are prepared by uniformly and intimately bringing into association the peptide with liquid carriers or finely divided solid carriers or both, and then if necessary shaping the product. The invention extends to methods for preparing a pharmaceutical composition comprising bringing a peptide as defined above in conjunction or association with a pharmaceutically or veterinary acceptable carrier or vehicle.

Formulations for oral administration in the present invention may be presented as: discrete units such as capsules, sachets or tablets each containing a predetermined amount of the active agent; as a powder or granules; as a solution or a suspension of the active agent in an aqueous liquid or a non-aqueous liquid; or as an oil-in-water liquid emulsion or a water in oil liquid emulsion; or as a bolus etc.

For compositions for oral administration (e.g. tablets and capsules), the term "acceptable carrier" includes vehicles such as common excipients e.g. binding agents, for example syrup, acacia, gelatin, sorbitol, tragacanth, polyvinylpyrrolidone (Povidone), methylcellulose, ethylcellulose, sodium carboxymethylcellulose, hydroxypropylmethylcellulose, sucrose and starch; fillers and carriers, for example corn starch, gelatin, lactose, sucrose, microcrystalline cellulose, kaolin, mannitol, dicalcium phosphate, sodium chloride and alginic acid; and lubricants such as magnesium stearate, sodium stearate and other metallic stearates, glycerol stearate, stearic acid, silicone fluid, talc waxes, oils and colloidal silica. Flavouring agents such as peppermint, oil of wintergreen, cherry flavouring and the like can also be used. It may be desirable to add a colouring agent to make the dosage form readily identifiable. Tablets may also be coated by methods well known in the art.

A tablet may be made by compression or moulding, optionally with one or more accessory ingredients. Compressed tablets may be prepared by compressing in a suitable machine the peptide in a free-flowing form such as a powder or granules, optionally mixed with a binder, lubricant, inert diluent, preservative, surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active agent.

Other formulations suitable for oral administration include lozenges comprising the peptide in a flavoured base, usually sucrose and acacia or tragacanth; pastilles comprising the peptide in an inert base such as gelatin and glycerin, or sucrose and acacia, and mouthwashes comprising the active agent in a suitable liquid carrier.

For topical application to the skin, the peptide may be made up into a cream, ointment, jelly, solution or suspension etc. Cream or ointment formulations that may be used for the drug are conventional formulations well known in the art, for example, as described in standard text books of pharmaceutics such as the British Pharmacopoeia.

Parenteral formulations will generally be sterile.

Throughout the description and claims of this specification, the word "comprise" and variations thereof, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith. Moreover, unless stated otherwise, any feature disclosed herein may be replaced by an alternative feature serving the same or a similar purpose.

BRIEF DESCRIPTION OF THE DRAWING FIGURES

Figure 1:
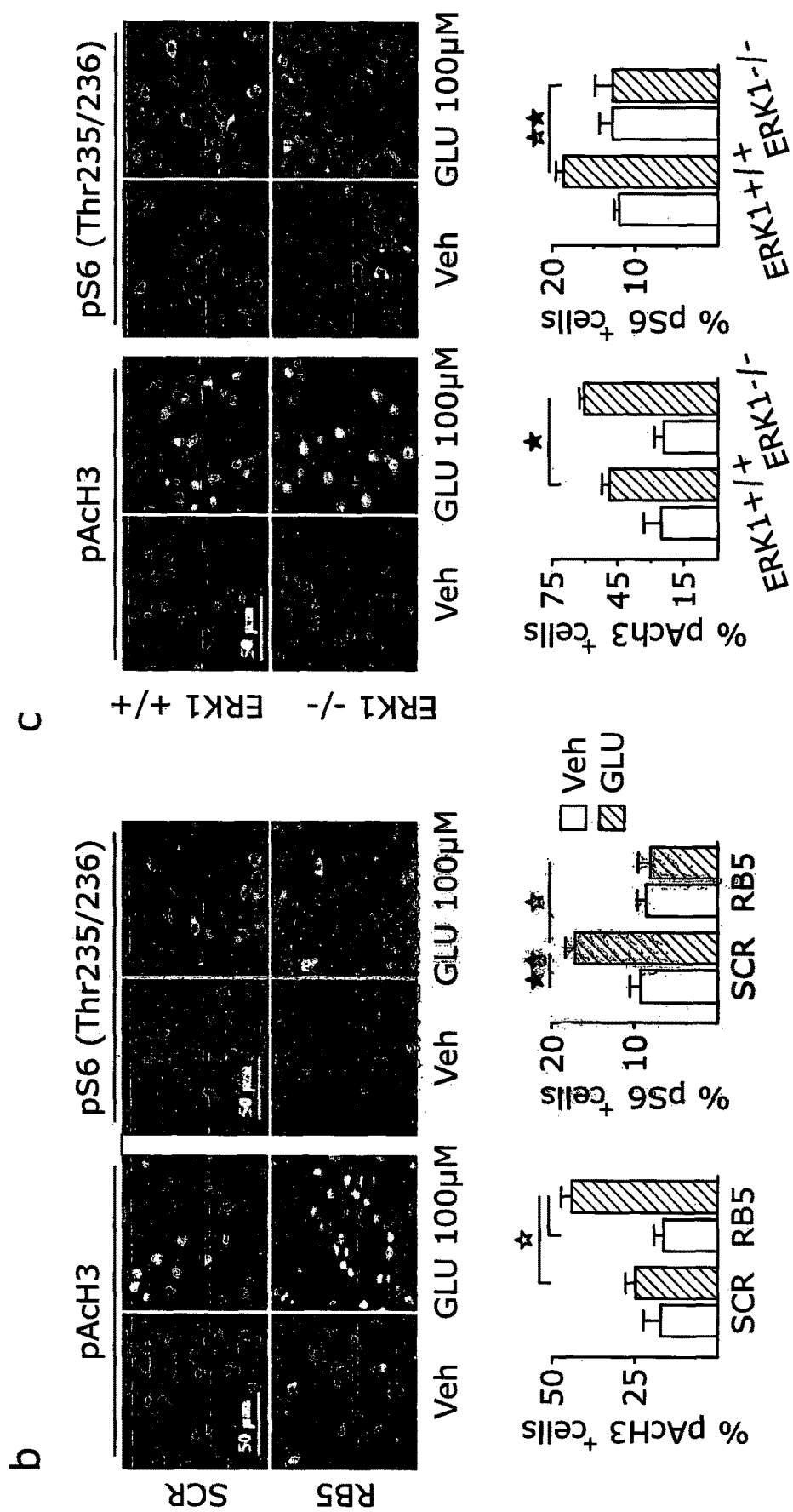
Figure 1:
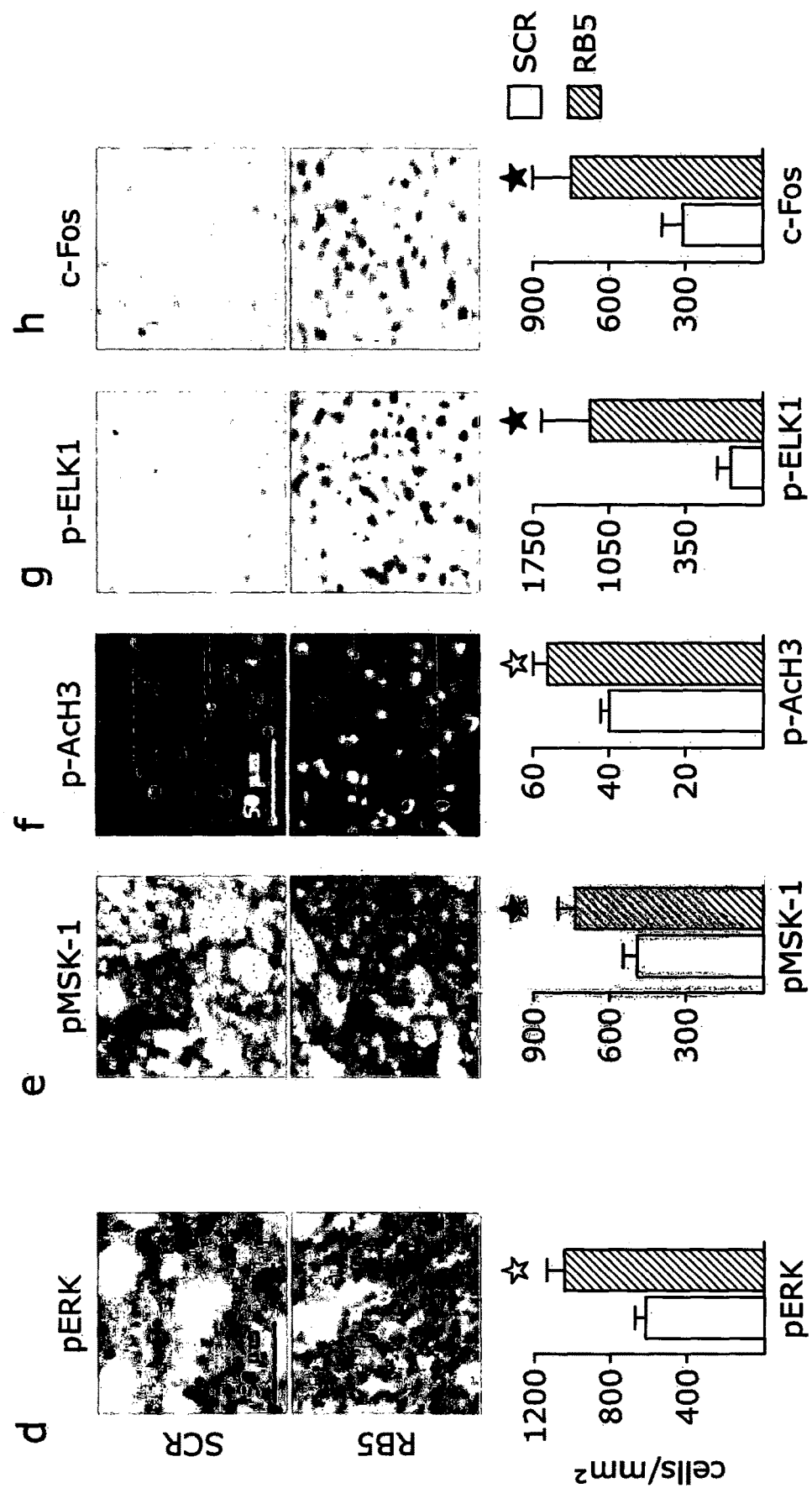
Figure 1:
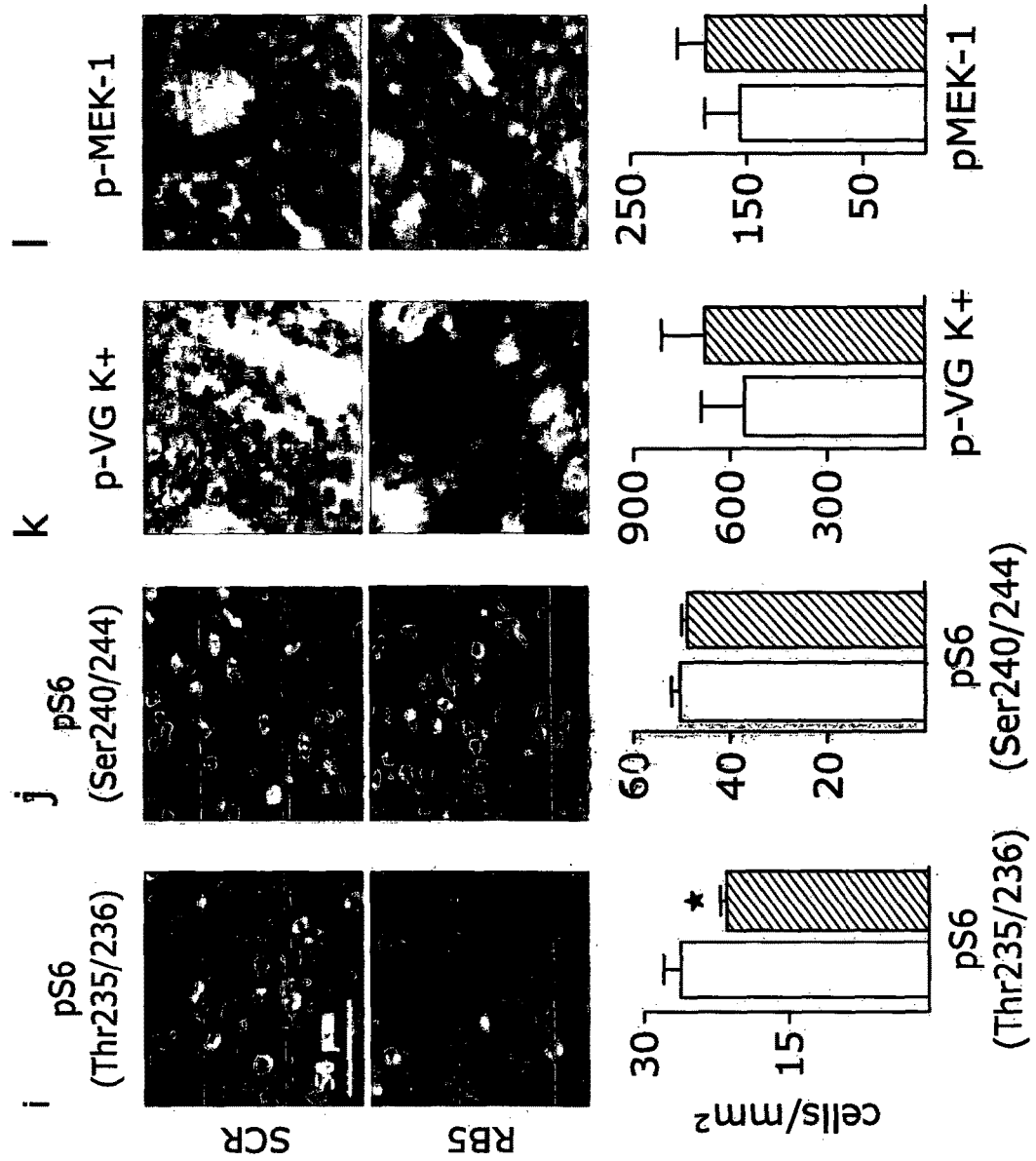
Figure 1:
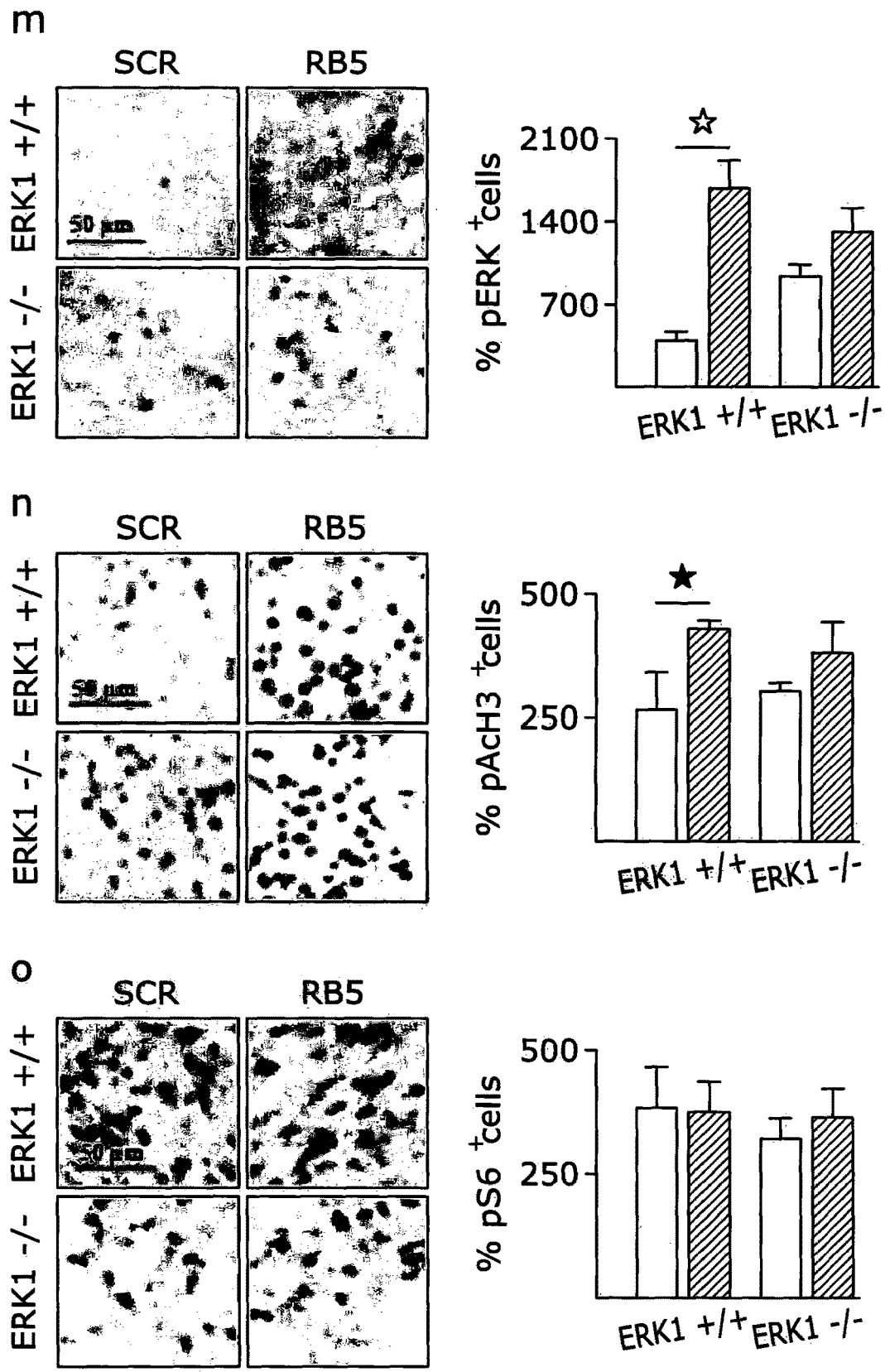
Figure 1:
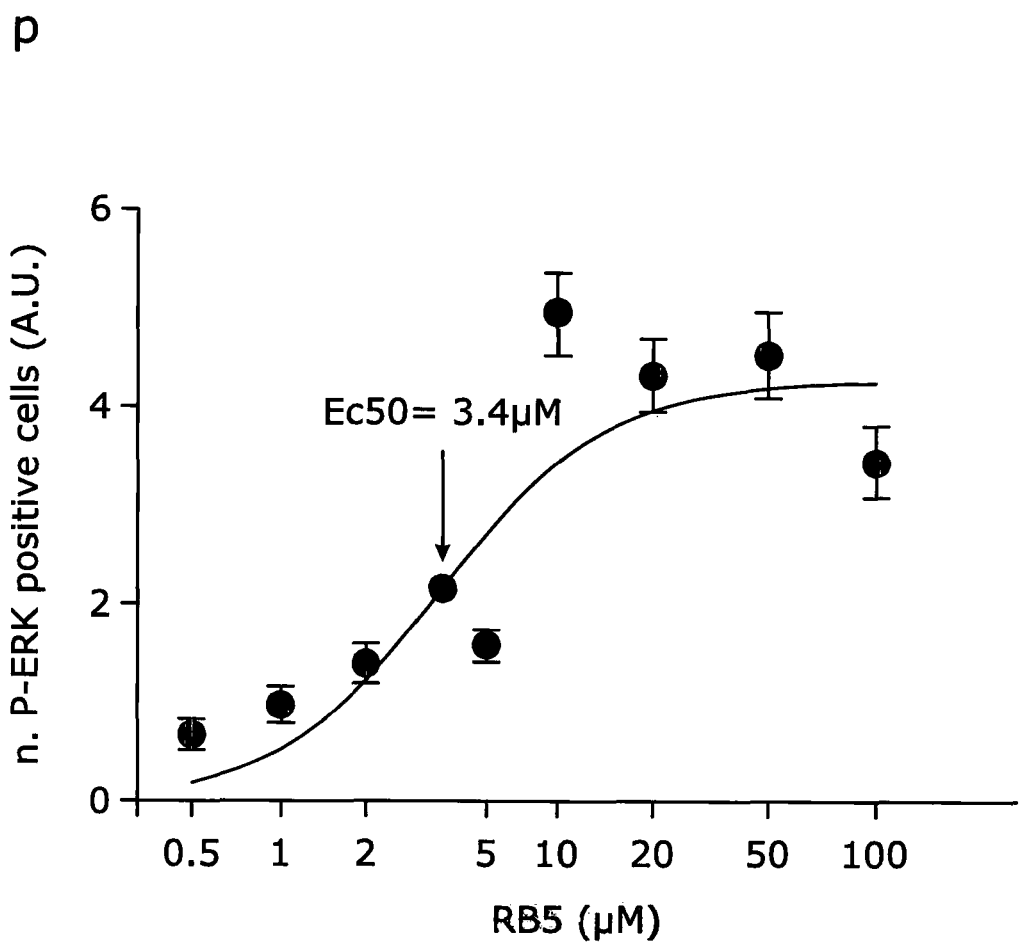

The invention will now be described by way of example only with reference to the Examples below and to the following Figures wherein:

FIG. 1. RB5 selectively stimulate nuclear ERK Signalling a) RB5 peptide selectively promoted activation of ERK2. Acute striatal slices either pre-treated with Scramble (SCR) or RB5 peptide (50 µM) and then stimulated 10 minutes with glutamate (GLU) (100 µM) or vehicle were analysed in Western blot (left panel) and probed with anti phospho ERK antibodies (p44$^{ERK1}$ and p42$^{ERK2}$) and anti ERK1/2 antibody. GAPDH was used as loading control. (Right panel) Quantifications demonstrate that pERK1 was equally increased in SCR and RB5 treated slices. Notably, ERK2 activation is significantly higher in RB5 treated sample in comparison to SCR slices. No changes were detected in the total ERK1 and ERK2 levels. GAPDH was used as loading control. Data are expressed as Mean±SEM (n=4). b-c) RB5 selectively enhanced nuclear signalling in response to glutamate, resembling the same phenotype found in ERK1 KO cells. b) The anti-phospho (Ser10)-acetyl(Lys14)-histone-H3 (green) and anti-NeuN (red) immunofluorescence on acute slices pre-treated with CPP-SCR or CPP-RB5 peptide (50 µM) and stimulated with glutamate (100 µM) showed a massive intra-nuclear MAPKs substrate activation due to CPP-RB5 peptide (Mean±SEM, n=15). The anti-phospho-S6 ribosomal protein (Thr235/236) immunofluorescence (green) and anti-NeuN (red) showed that CPP-RB5 peptide had no effect on cytosolic MAPKs substrate (Mean±SEM, n=15). c) Same effects were found using slices from ERK1 KO mice and their WT controls treated with glutamate (Mean±SEM, n=13). d-l) CPP-RB5 actively promotes nuclear signalling after a single injection in vivo. Mice injected with a single dose of CPP-SCR or CPP-RB5 peptides (20 mg/kg, i.p.) were rapidly perfused 1 h later and brains were dissected and further analysed for IHC and immunofluorescence. Representative photomicrographs of pERK1/2, pMSK, pAch3, pELK1 and c-Fos expression in the striatum. RB5 peptide enhanced striatal ERK phosphorylation (d) and promoted a selective activation of nuclear ERK-dependent signalling and gene transcription (pMSK, pAcH3, pELK, c-Fos (e-h)). In contrast, RB5 did not influence the phosphorylation of the cytoplasmic markers (pMEK-1, pVGK+, pS6). m-o) a single administration of RB5 induced a significant activation of pERK and pAcH3 in ERK1 WT mice while this effect did not reach the statistical significance in ERK1 KO mice suggesting that RB5 acts like ERK1 inhibitor. As additional control we showed that phosphorylation of S6 was comparable in both genotypes confirming that RB5 preferentially activates nuclear signalling. Two-way ANOVA Bonferroni post hoc comparison: one black star, $p<0.05$, two black stars, $p<0.01$, one white star, $p<0.001$. p) Dose response curve of RB5 peptide for ERK activation. 200 μm thick striatal slices were freshly prepared from 2-month old mice and transferred into a perfusion chamber for 1 h at 32° C. Slices were pre-treated with different doses of RB5 or scrambled control. After 1 h, slices for each dose was fixed in PFA 4% for 15 min. 18 μm cryo-sections were processed for immunohistochemistry with anti-phospho p44/p42 MAP kinase. Neuronal quantification was performed with ImageJ software by counting the number of phospho-ERK positive cells in each slice. The level of activation is expressed on the Y-axis as arbitrary units (AU). Doses are reported in a logarithmic scale (Log 10) on the X-axis. The EC50 was calculated using GraphPad Prism software. RB5 was effective in enhancing pERK with an EC50 of 3.4 μM.

Figure 2:
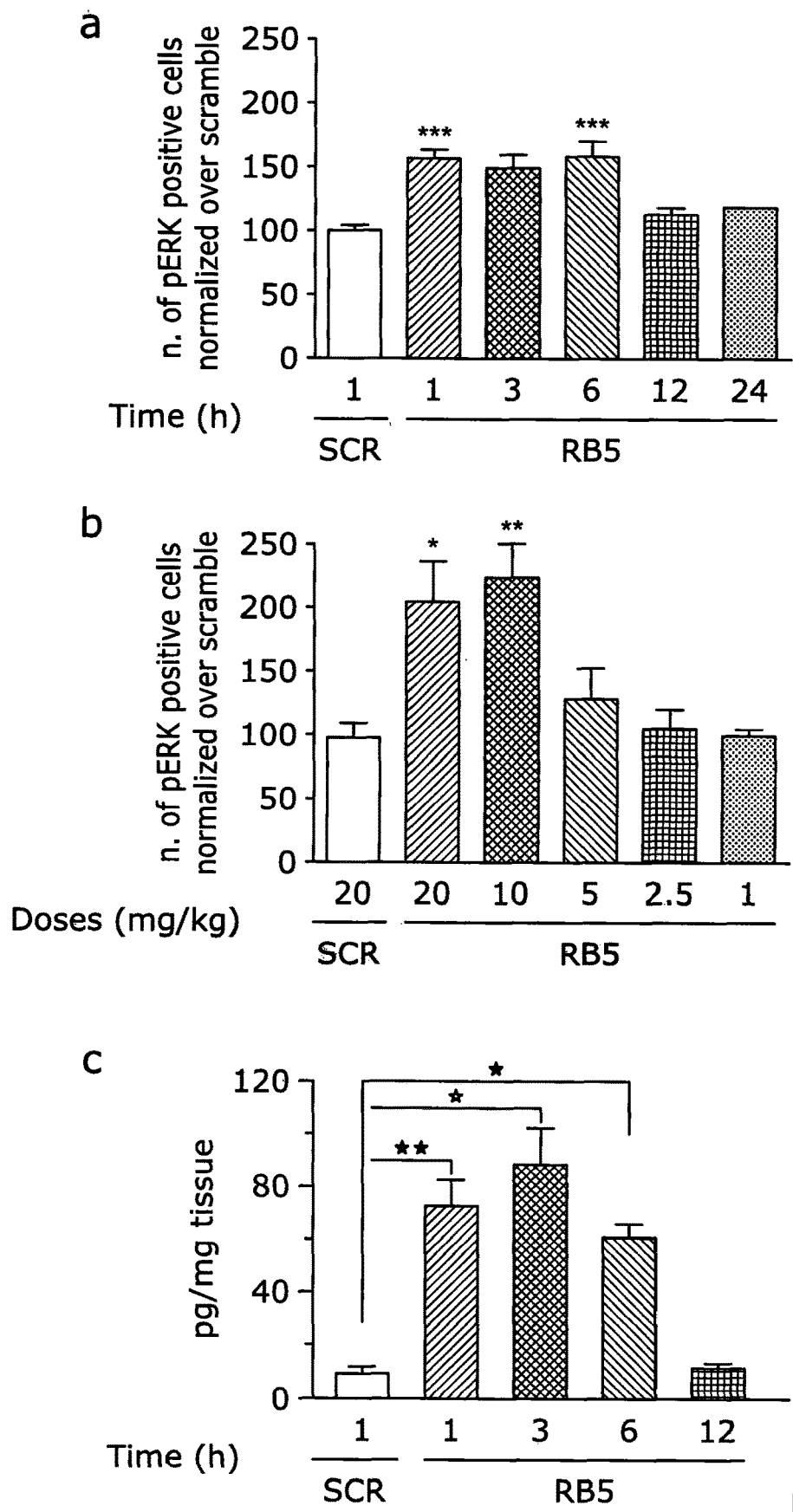

FIG. 2. Time course and dose response studies for RB5 on ERK activation.

a) Wild type mice (n=5 each group) were injected with RB5 (20 mg/kg, i.p.) or scramble inactive peptide (SCR, 20 mg/kg, i.p.). Mice injected with RB5 were perfused at different time points, whereas scramble-injected mice were perfused after 1 hour. Immunohistochemical analysis was carried out against phospho-p44/p42 MAP kinase (Thr202/Tyr204). Quantification of phospho-ERK positive cells in the dorsal striatum shows that phospho-ERK levels were significantly increased up to 6 hours after the injection of RB5 and they returned to the basal levels after 12 h hours. One-way ANOVA $F_{5,29}=9.137$, $p<0.0001$. Bonferroni's post-hoc test, SCR vs RB5 1 h: $p<0.001$, SCR vs RB5 6 h: $p<0.001$. Data are expressed as Mean±SEM. b) Wild type mice (n=5 each group) were systemically injected with different doses of RB5 or with 20 mg/kg of scramble inactive peptide (SCR) and perfused 1 hour after. Immunohistochemical analysis was carried out against phospho-p44/p42 MAP kinase (Thr202/Tyr204). Quantification of phospho-ERK positive cells in the dorsal striatum shows that RB5 activate ERK in a dose-dependent manner. One-way ANOVA: $F_{5,29}=7.097$, $p<0.001$. Bonferroni's post-hoc test, SCR vs RB5 20 mg/kg: $p<0.05$, SCR vs RB5 10 mg/kg: $p<0.01$. Data are expressed as Mean±SEM. c) RB5 brain levels measured with mass spectrometry at different hours after a single i.p. administration of 20 mg/kg. High levels of RB5 were detected up to 6 hrs (one-way ANOVA, $F_{4,18}=17.469$, $P<0.0001$, Bonferroni's post-hoc, SCR vs RB5 1 h $P<0.01$, SCR vs RB5 3 h $P<0.0001$, SCR vs RB5 6 h $P<0.05$). Results show mean±s.e.m. White star $P<0.0001$, $P<0.001$, $P<0.01$, $P<0.05$.

Figure 3:
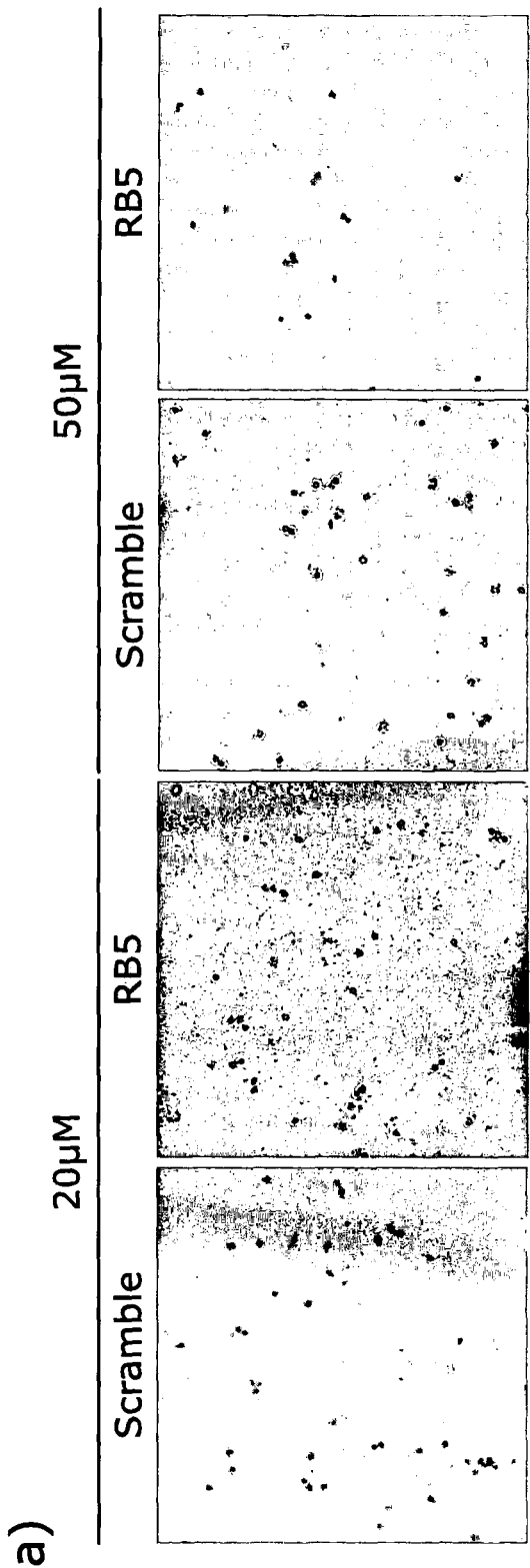
Figure 3:
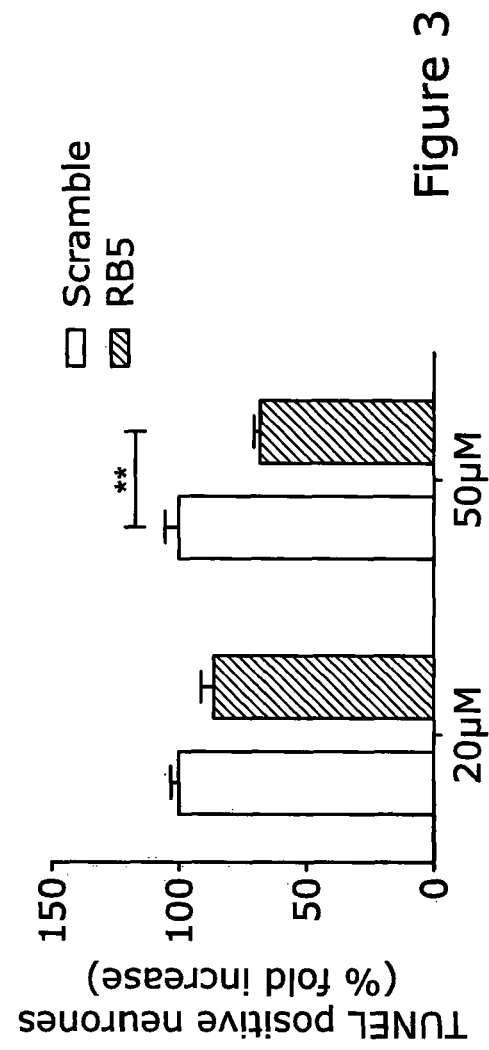

FIG. 3. RB5 attenuated neuronal cell death in embryonic striatal cultures

Neuronal embryonic striatal cultures (E17) were exposed for 7 days to Scramble or RB5 peptide containing medium (two final concentrations of 20 μM or 50 μM. a) Representative micrographs showing TUNEL labelling of striatal neurons. b) Quantification of apoptotic nuclei stained in dark showed a significant reduction of apoptotic levels in cultures treated with higher dose of RB5 ($p<0.01$). Data are expressed as Mean±SEM, n=5. Two-way ANOVA Bonferroni post-hoc comparison **$p<0.01$.

Figure 4:
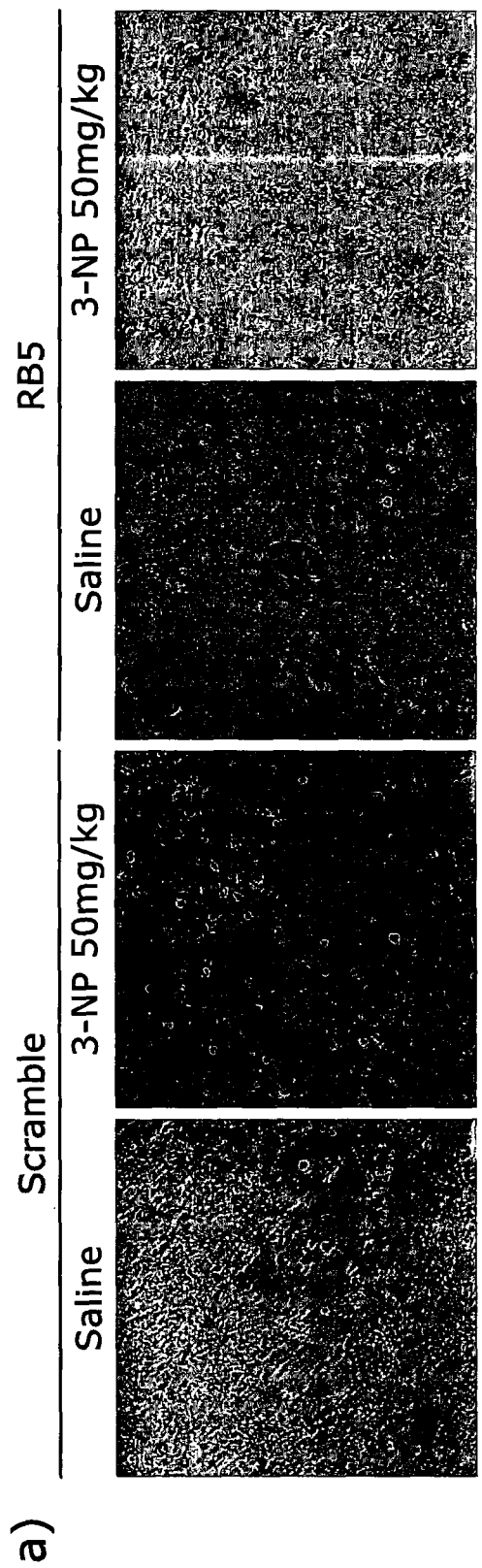
Figure 4:
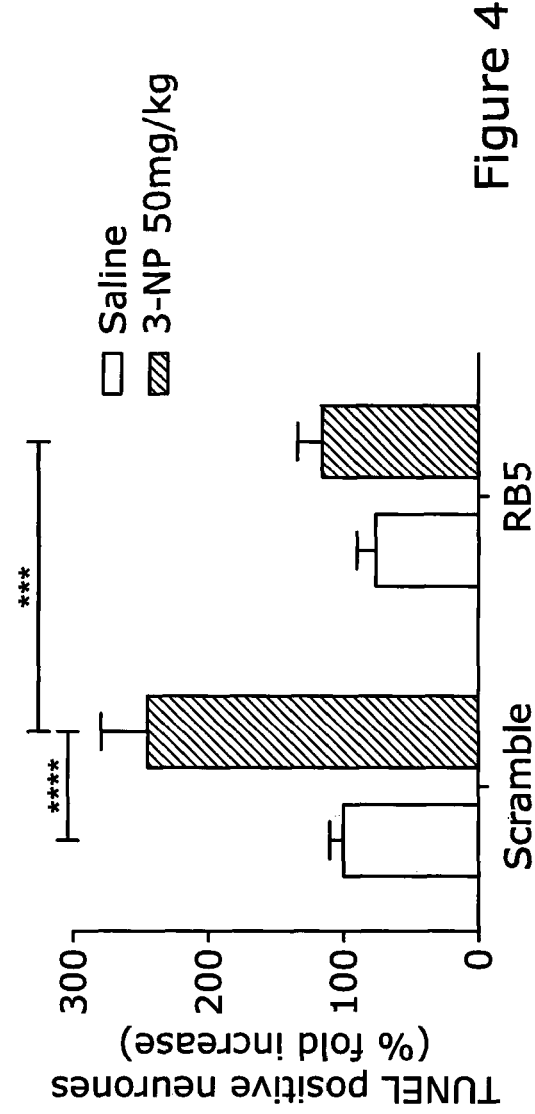
Figure 4:
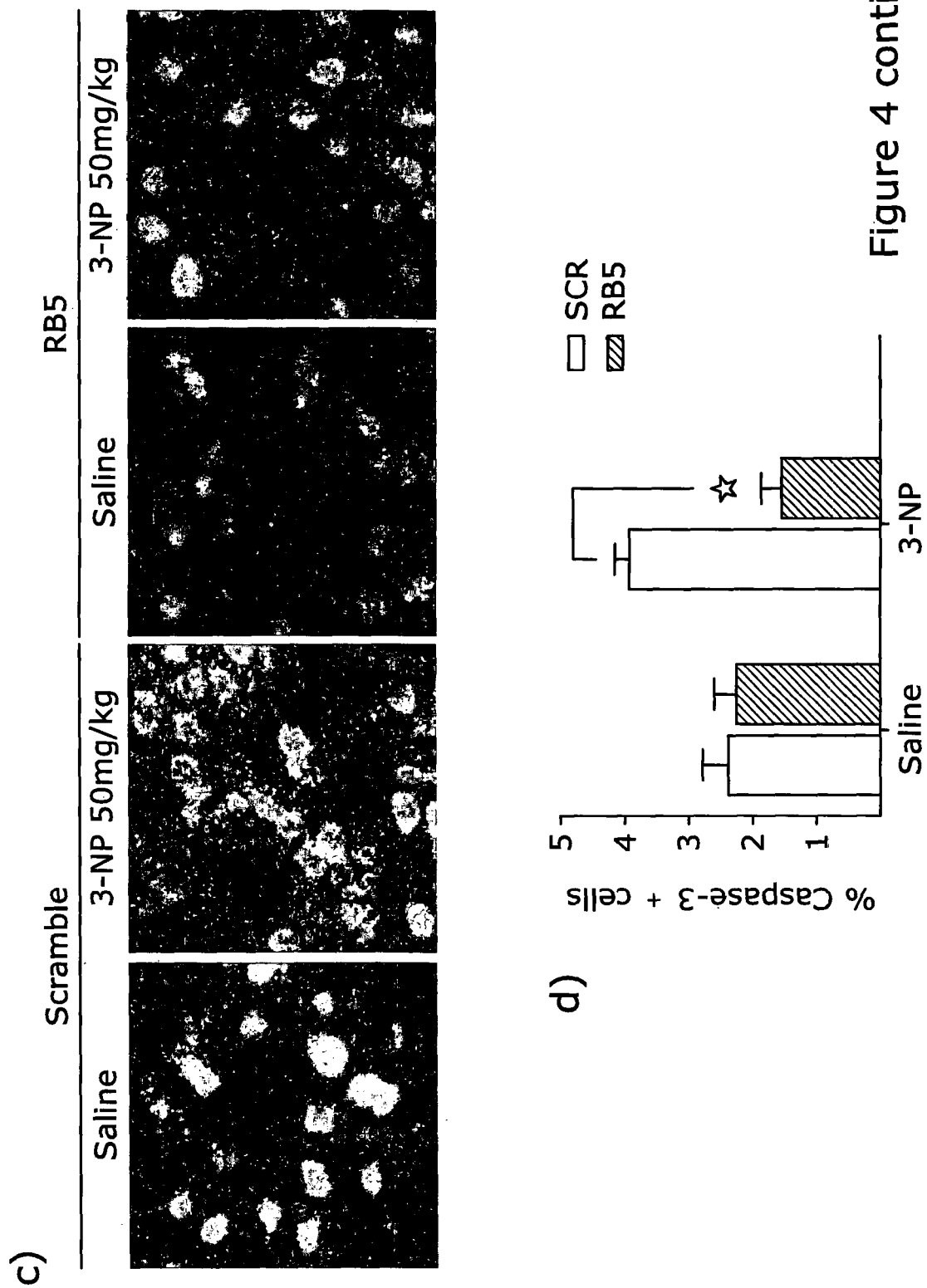

FIG. 4. RB5 attenuated neuronal cell death in a pharmacological mouse model (3-Nitropropionic acid; 3-NP) of Huntington's disease a) TUNEL staining from striatum of C57BL/6 mice injected twice a day with Scramble or RB5 peptides (20 mg/kg, i.p.) and once with saline or 3-NP (50 mg/kg, i.p.) for 7 consecutive days. b) Mice co-treated with RB5 peptide and 3-NP showed a significant reduction of apoptotic levels compared to mice co-treated with Scramble peptide and 3-NP. Importantly, this reduction resembled physiological condition (RB5 3-NP vs RB5 Saline $p=0.85$). Mean±SEM, n=10 each experimental group). Two-way ANOVA Bonferroni post-hoc comparison *$p<0.001$**$p<0.0001$. c) Caspase-3 immunofluorescence in the striatum of mice co-treated either with Scramble or RB5 peptide (20 mg/kg, i.p., twice a day) and with saline or 3-NP (50 mg/kg, i.p., once a day) for 7 consecutive days. d) Mice co-treated with RB5 peptide and 3-NP showed diminished Caspase-3 levels (two-way ANOVA, Bonferroni's post-hoc, White star $P<0.0001$).

Figure 5:
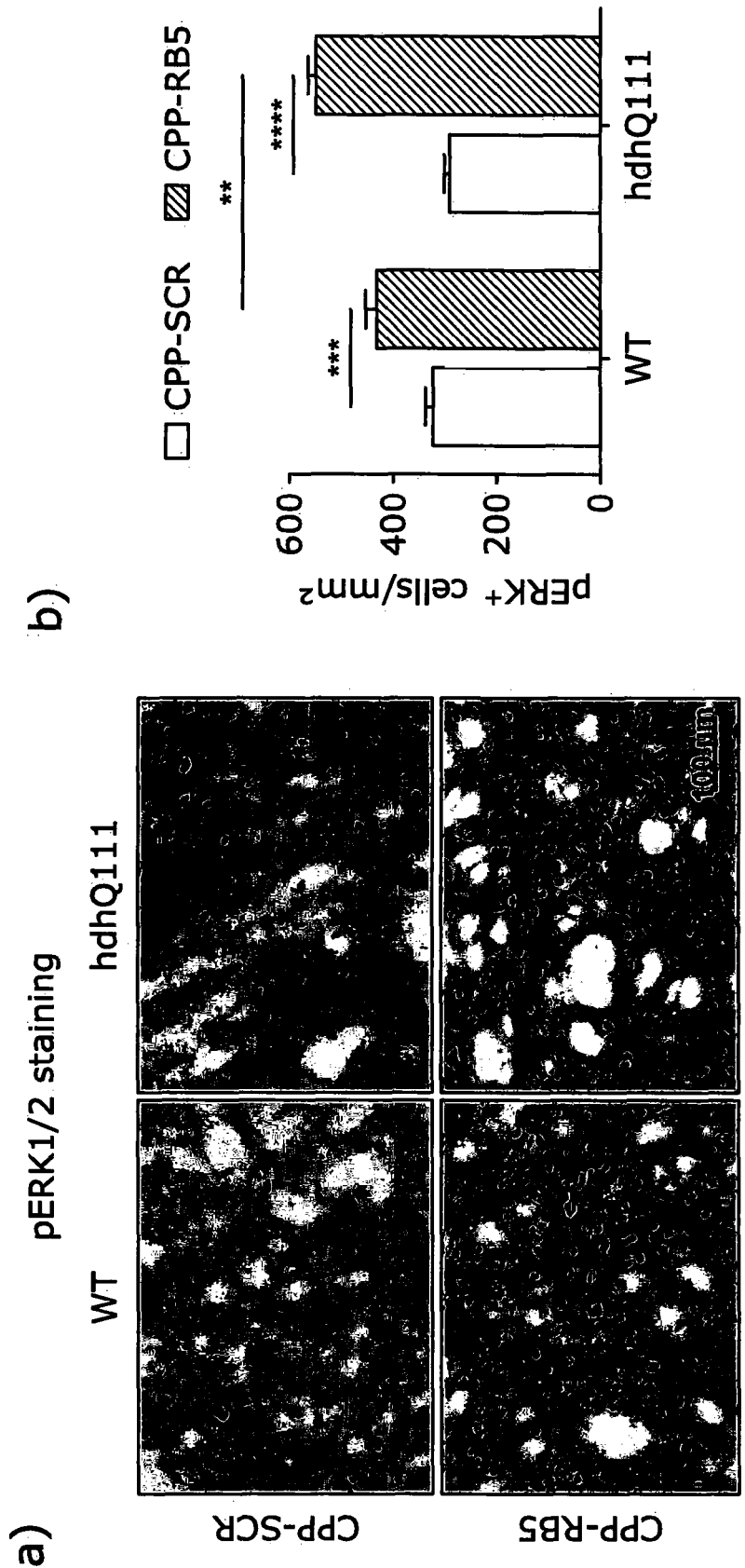
Figure 5:
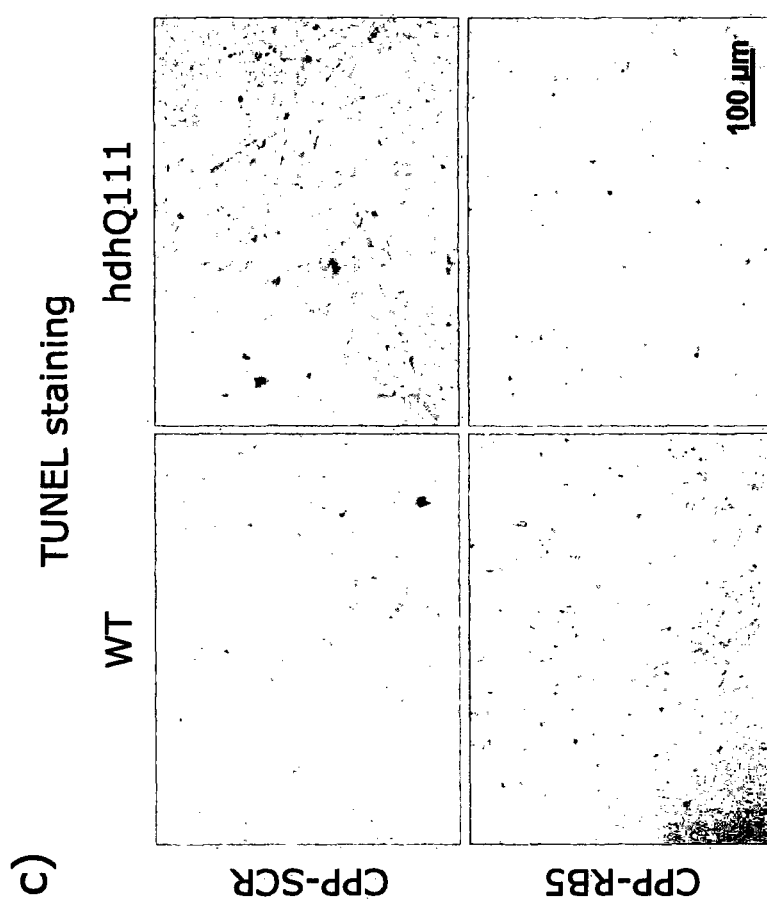
Figure 5:
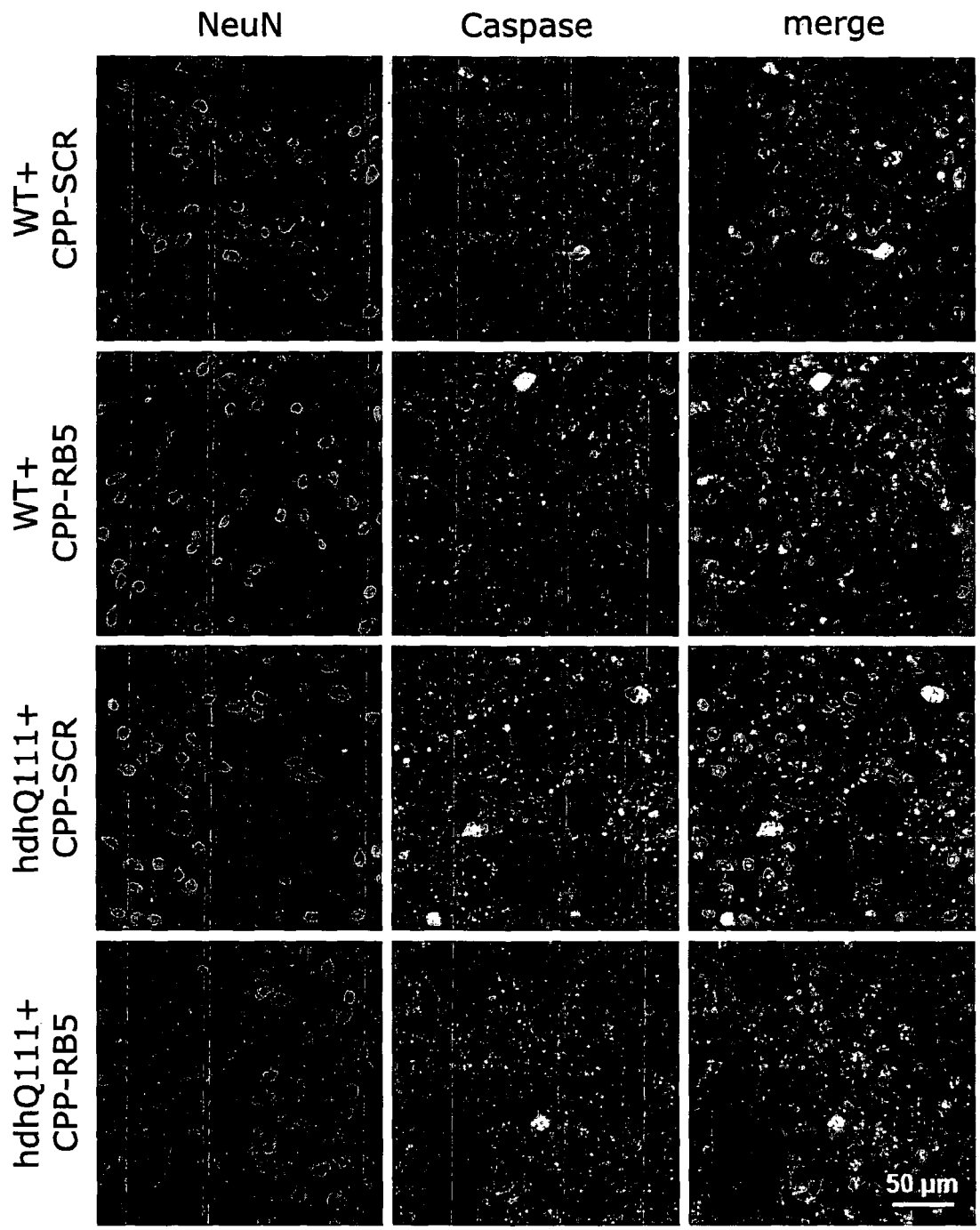
Figure 5:
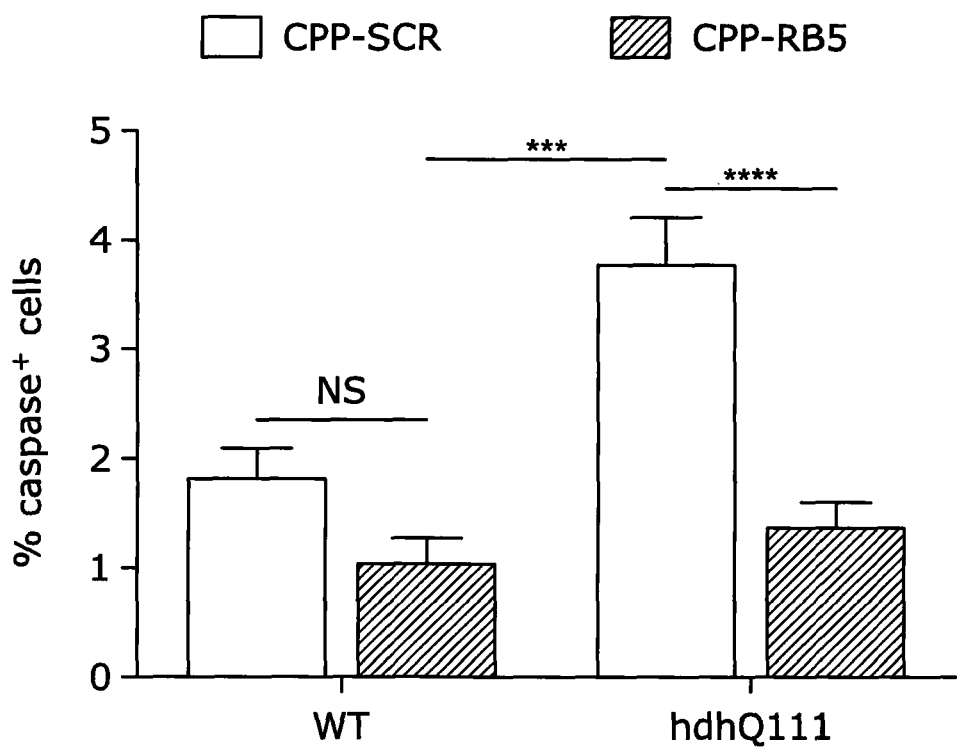

FIG. 5. RB5 shows neuroprotective effect in a genetic mouse model (HdhQ111) of Huntington's disease WT and HdhQ111 mice were treated with CPP-RB5 or Scramble (CPP-SCR) peptides (20 mg/kg i.p.) for 8 days.

a) Representative pictures of ERK1/2 phosphorylation in dorsolateral striatum of WT and HdhQ111 mice. b) HdhQ111 mice treated with RB5 peptide showed a significant enhancement of ERK activation in comparison to their littermates. Two-way ANOVA Bonferroni post-hoc comparison $p<0.01$*$p<0.001$**$p<0.0001$. c) Representative pictures of TUNEL staining in dorsal striatum of WT and HdhQ111 mice. d) HdhQ111 mice treated with RB5 peptide showed a significant reduction of apoptotic cells compared to Scramble treated mice. Two-way ANOVA Bonferroni post-hoc comparison $p<0.01$. e) Representative pictures of Cleaved Caspase-3 immunofluorescence staining. f) A significant reduction of pre-apoptotic state was observed in hdhQ111 mice treated with RB5. Two-way ANOVA Bonferroni post-hoc comparison ***$p<0.001$.

Figure 6:
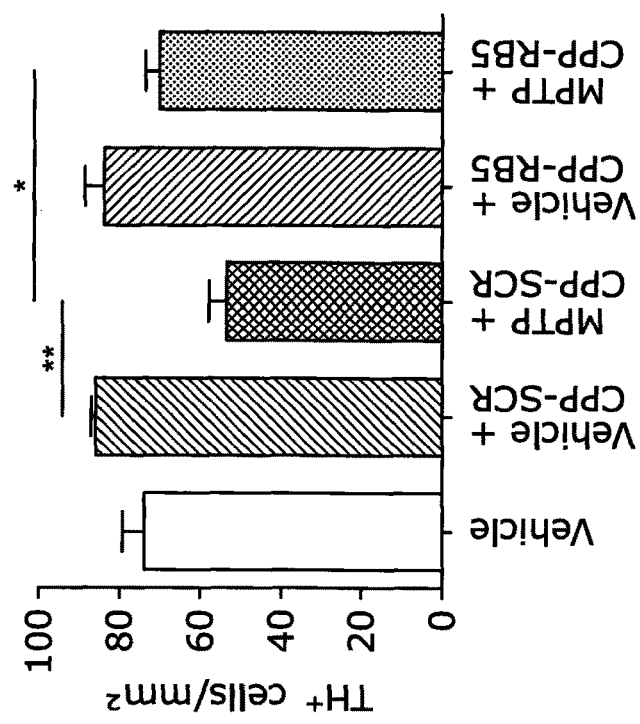
Figure 6:
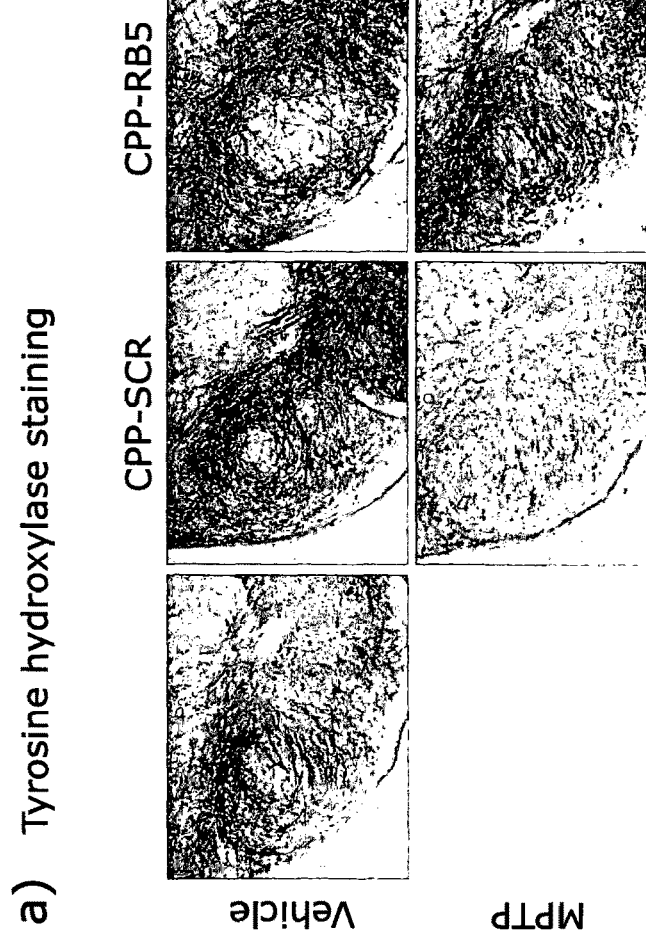
Figure 6:
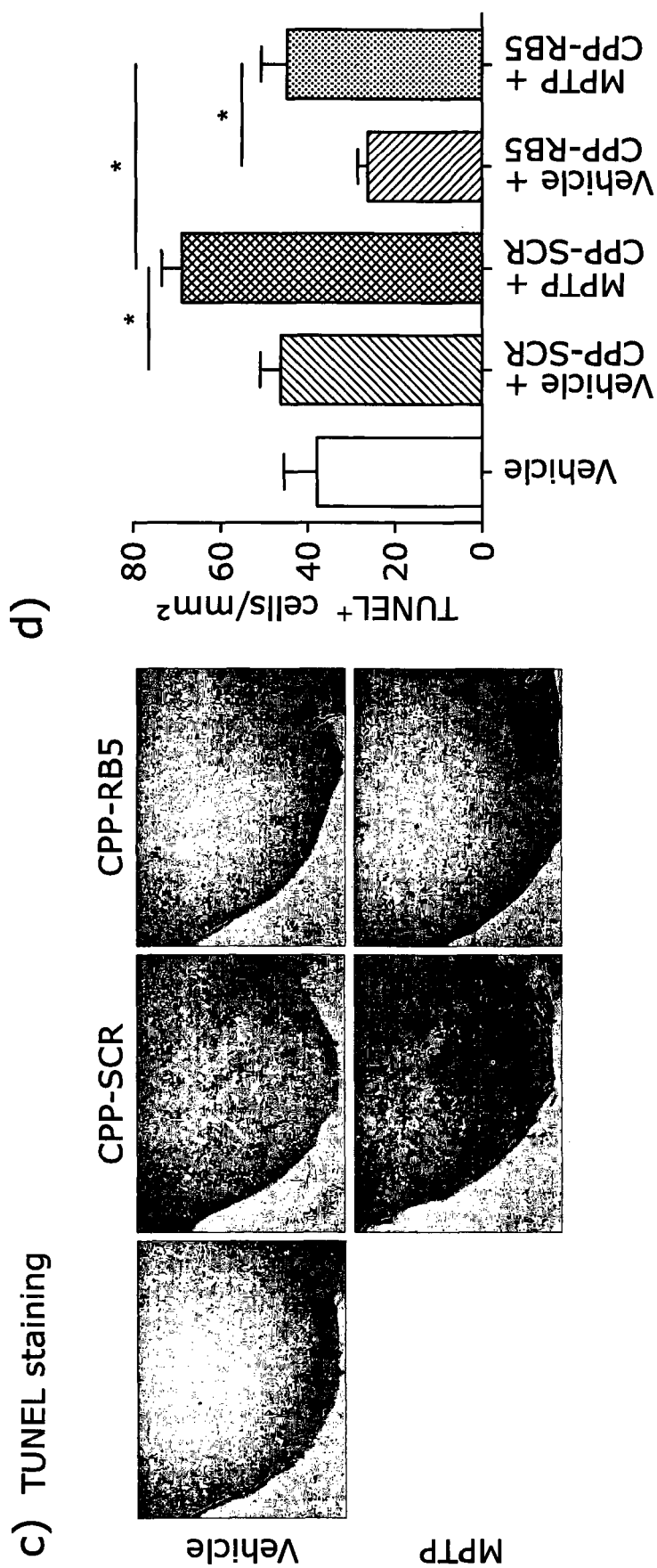
Figure 6:
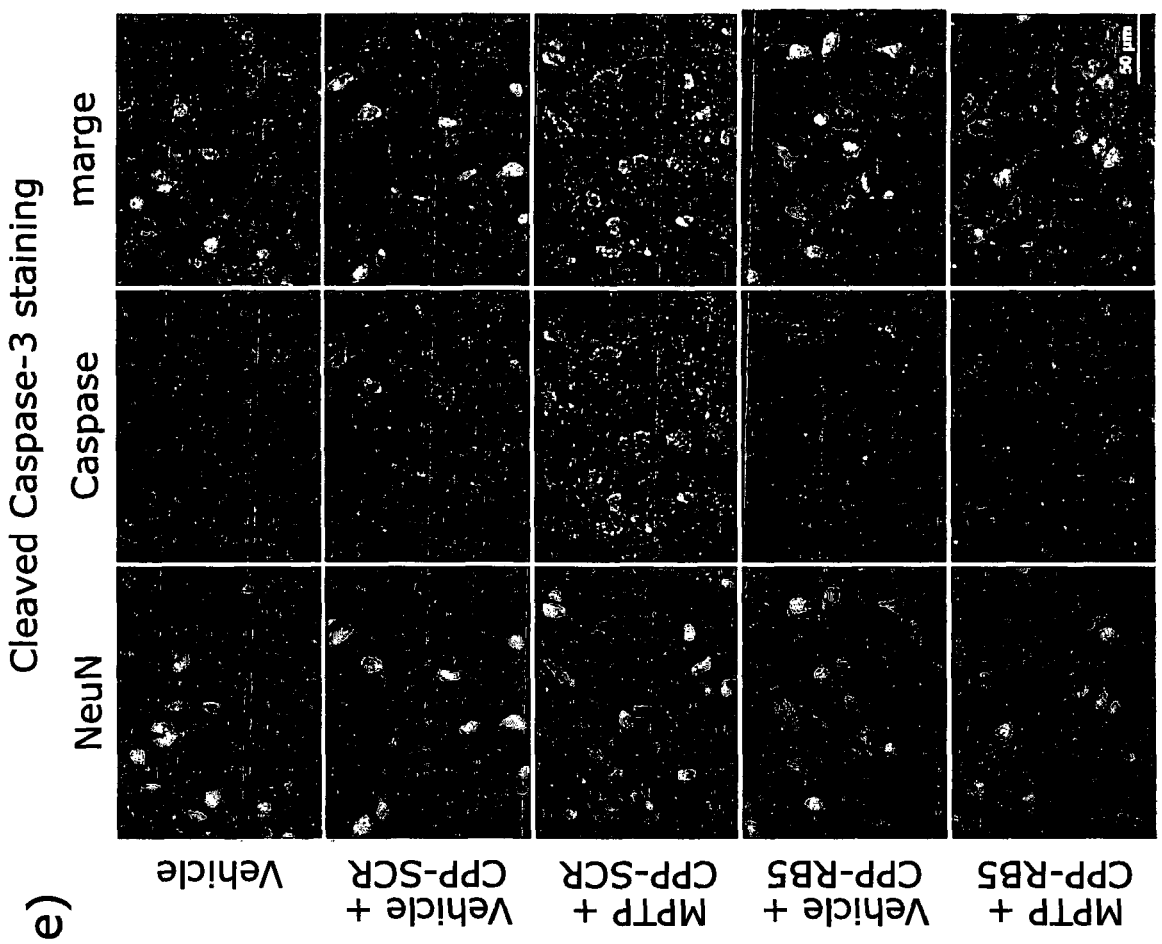

FIG. 6: RB5 shows neuroprotective effect in the subacute MPTP (1-methyl-4-phenyl-1,2,3,6-tetrahydropryridine) mouse model of Parkinson's Disease Adult mice were treated with MPTP or vehicle (20 mg/kg i.p.) for 4 days. CPP-RB5 or Scramble (CPP-SCR) peptides (20 mg/kg i.p.) were injected 1 h before MPTP/Vehicle. a) representative pictures of TH in Substantia Nigra. b) mice co-treated with RB5 peptide and MPTP showed a significant reduction of TH loss compared to Scramble peptide treated group. Two-way ANOVA Bonferroni post-hoc comparison *p<0.05**p<0.01.

c) representative pictures of TUNEL staining in nigral neurones. d) mice co-treated with RB5 peptide and MPTP showed a significant reduction of apoptotic cells compared to Scramble treated mice. Two-way ANOVA Bonferroni post-hoc comparison *p<0.05. e) representative pictures of Cleaved Caspase-3 immunofluorescence staining. f) a significant reduction of the pre-apoptotic state was observed in MPTP mice pre-treated with RB5 peptide. Two-way ANOVA Bonferroni post-hoc comparison *p<0.05**p<0.01

Figure 7:
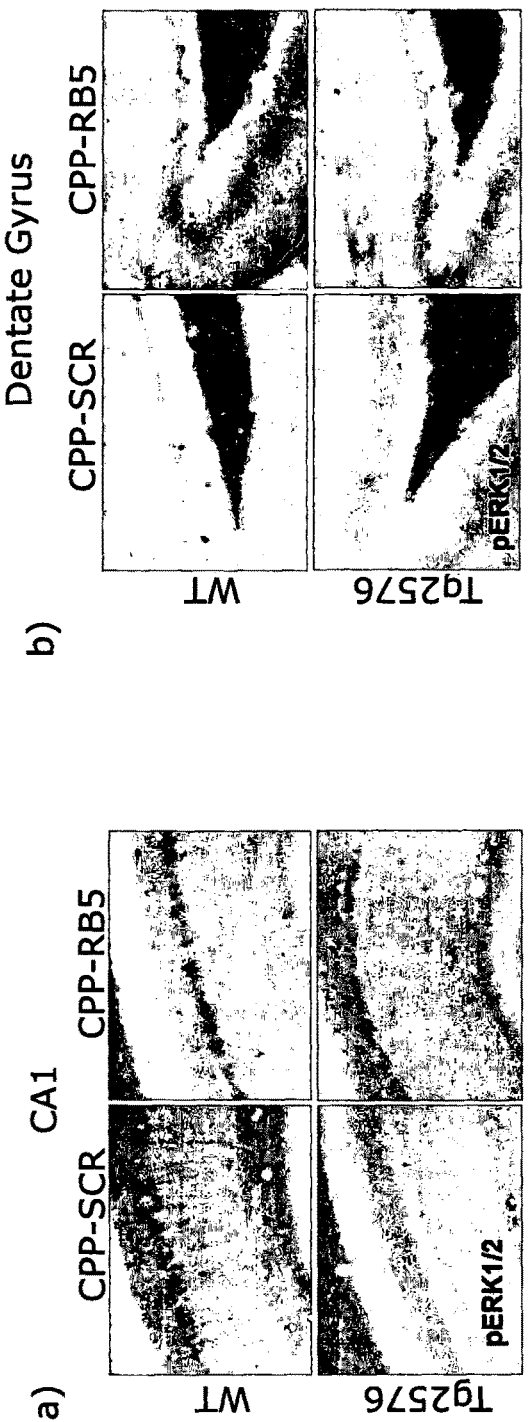
Figure 7:
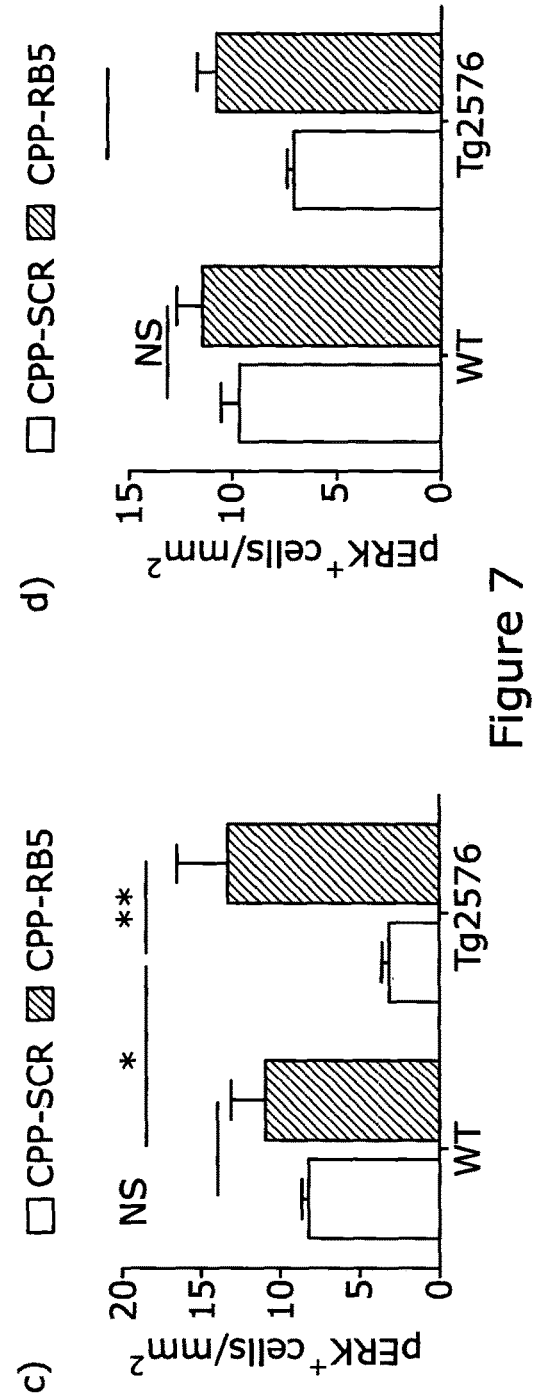
Figure 7:
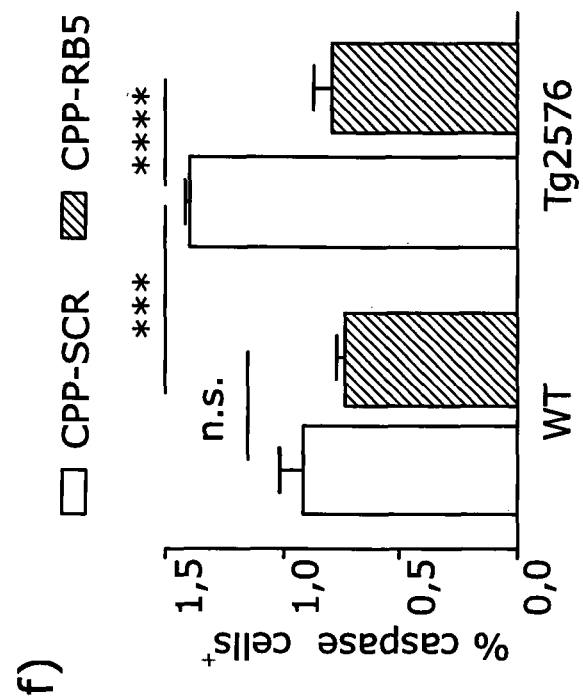
Figure 7:
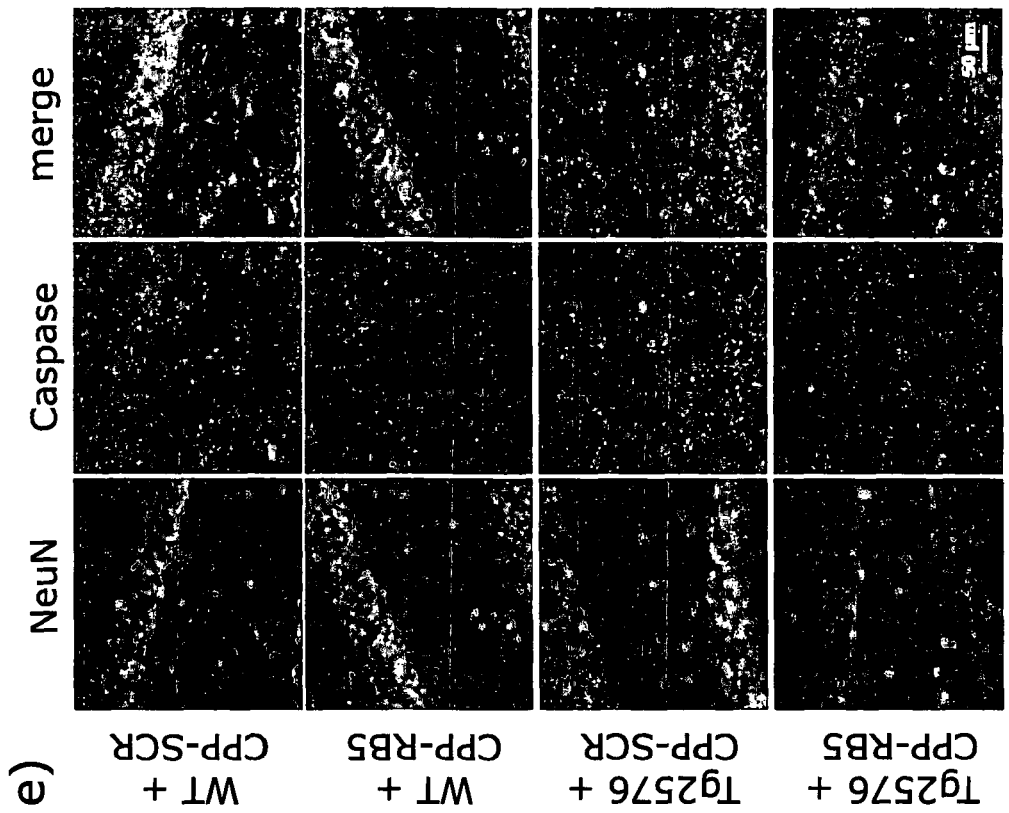

FIG. 7. RB5 peptide shows neuroprotective effect in the Tg2576 mouse model of Alzheimer's Disease WT and Tg2576 mice were treated with RB5 or Scramble peptides (20 mg/kg i.p.) for 7 days. a) Representative pictures of ERK1/2 phosphorylation in the CA1 and b) Dentate Gyrus (DG) of hippocampal region of WT and Tg2576 mice. c-d) A significant enhancement of ERK activation was observed in Tg2576 mice treated with RB5 peptide in comparison to Scramble treated mice. Two-way ANOVA, Bonferroni post-hoc comparison p<0.01*p<0.001 white star p<0.0001 e) Representative pictures of Cleaved Caspase-3 immunofluorescence staining. f) A significant reduction of the pre-apoptotic state was observed in Tg2576 mice treated with RB5. Two-way ANOVA Bonferroni post-hoc comparison p<0.01*p<0.001.

Figure 8:
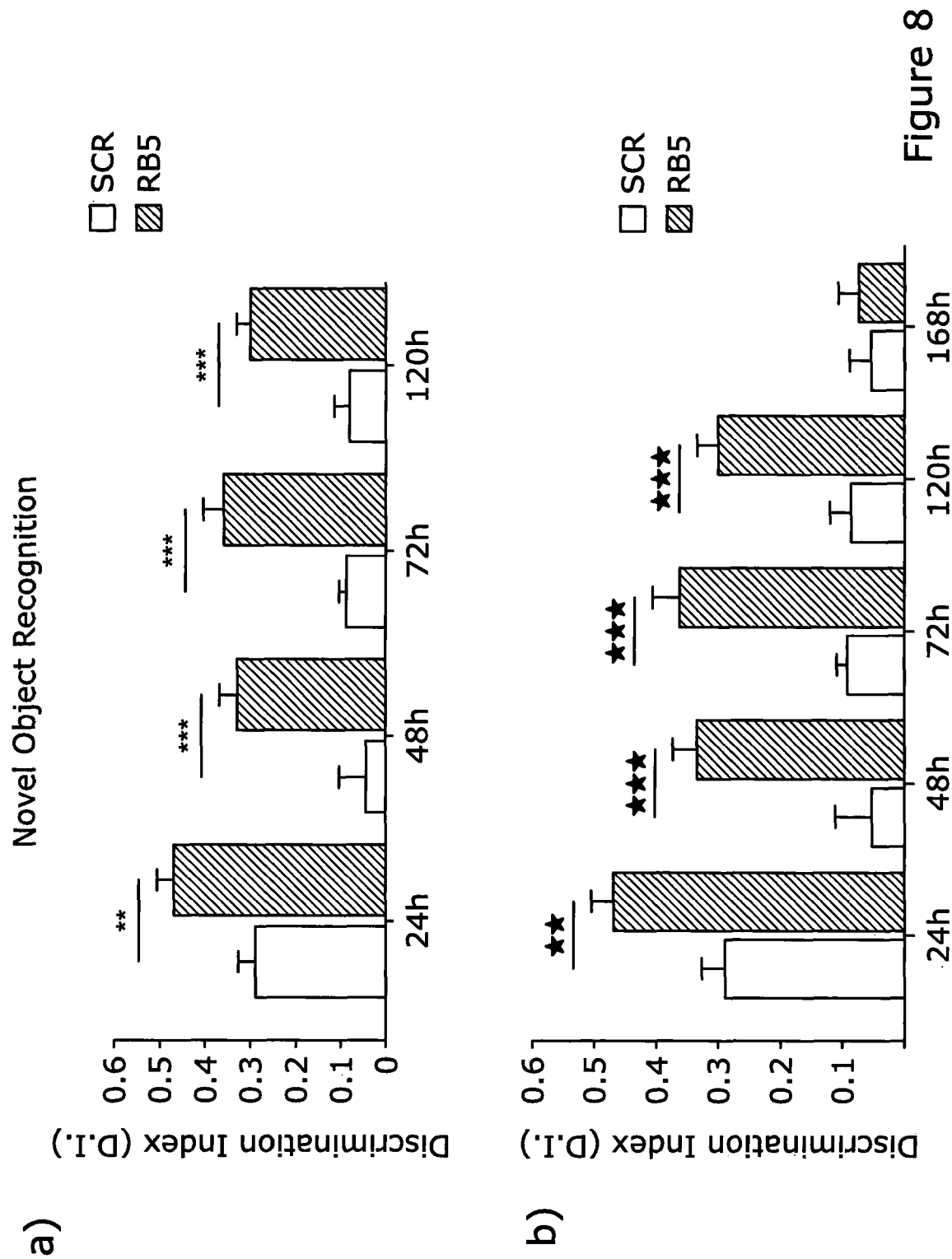

FIG. 8. RB5 enhances memory formation and consolidation in WT mice performing the Novel Object Recognition Test (NOR)

a) After a 5 min habituation session in the empty arena on day 1, mice were injected with RB5 (20 mg/kg) or vehicle one hour before the training session with two identical objects on day 2 and were then evaluated for their long-term memory on subsequent days. Discrimination Index (D.I.) was tested at different time points 24, 48, 72, and 120 hrs (a) and also up to 168 h (b). At 24 hours, D.I. of RB5 group was significantly higher than the Scramble group. On subsequent days, while the RB5 group remained high, the Scramble group returned to basal levels. *p<0.01**p<0.0001. RB5 significantly enhanced memory formation and consolidation in NOR up to 5 days. At 24 h, D.I. of RB5 group was highly significant (Independent sample t-test $t_{26}$=4.428 P<0.01, SCR (n=14) RB5 (=14)) as well as at 48 h (Independent sample t-test $t_{38}$=4.210 P<0.0001, SCR (n=18) RB5 (=22)). At 48 h D.I. of Scramble group drop below the chance level (One sample t-test SCR $t_{17}$=0.566 P=0.579) while D.I. of RB5 group was greatly above it (One sample t-test RB5 $t_{21}$=8.077 P<0.0001). At 72 h, D.I. of RB5 group remained highly significant (Independent sample t-test $t_{14}$=7.899 P<0.0001, SCR (n=7) RB5 (=9)) and above chance level (One sample t-test RB5 $t_6$=12.341 P<0.0001; SCR $t_6$=9.073 P<0.0001). At 120 h, D.I. of RB5 group was still highly significant (Independent sample t-test $t_{23}$=4.290 P<0.0001, SCR (n=10) RB5 (=15)) and above chance level (One sample t-test RB5 $t_{14}$=9.143 P<0.0001; SCR $t_9$=2.230 P=0.053). At 168 h, D.I. of RB5 group went down to basal levels indistinguishable from SCR group (Independent sample t-test $t_{18}$=0.777 P=0.447, SCR (n=10) RB5 (=10)). Results show mean±s.e.m. P<0.001, P<0.01.

Figure 9:
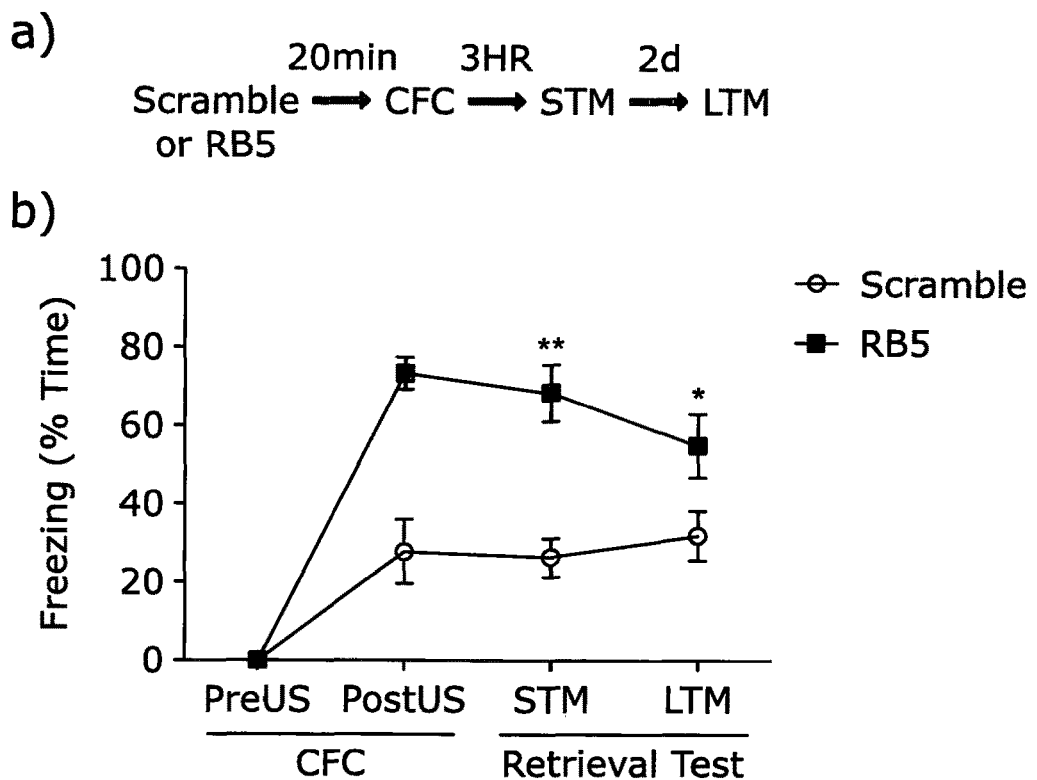

FIG. 9. RB5 enhances acquisition of Contextual Fear memory in healthy animals.

Awake rats were infused bilaterally via indwelling steel cannula aimed at the dorsal CA1 with either 2 mg/ml Scramble peptide (n=6) or RB5 (n=5) 20 min prior to conditioning. a) STM and LTM were assessed by measuring the conditioned fear behaviour (freezing) during a 2 min recall test 3 hr and 2 days after training, respectively. b) RB5 administration had a profound effect on the freezing behaviour of the rats (test×group, F (2.262,20.361)=9.439, e=0.754, P=0.000, repeated measures ANOVA). This manifested as an increase in the post footshock (postUS) freezing behaviour during fear conditioning ($F_{(1,9)}$=21.532, P=0.001, PreUS vs. postUS freezing behaviour X Infusion interaction, repeated measures ANOVA), and an increase in both STM and LTM. (*p<0.05, **p<0.01, FLSD test).

Figure 10:
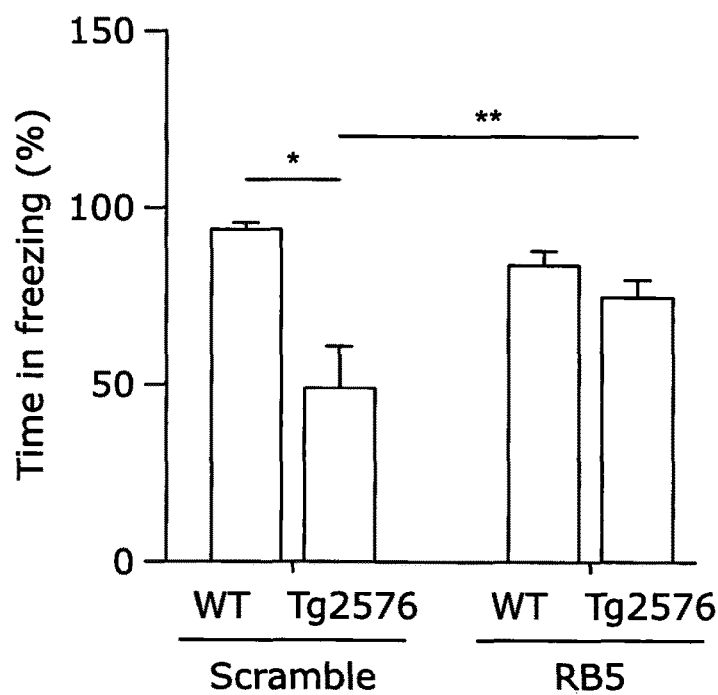

FIG. 10. RB5 enhances acquisition of Contextual Fear memory in Tg2576 mouse model of Alzheimer's Disease.

7 months old Tg2576 mice and WT mice were treated with either CPP-SCR or CPP-RB5 (20 mg/kg, i.p.) before Contextual Fear Conditioning (CFC) training and tested for memory retention 24 h later. Contextual Fear (CF) memory impairment in Tg2576 mice is fully rescued by RB5 treatment. Values are reported as % of time spent freezing. Data are expressed as Mean±SEM. *p<0.05**p<0.01.

Figure 11:
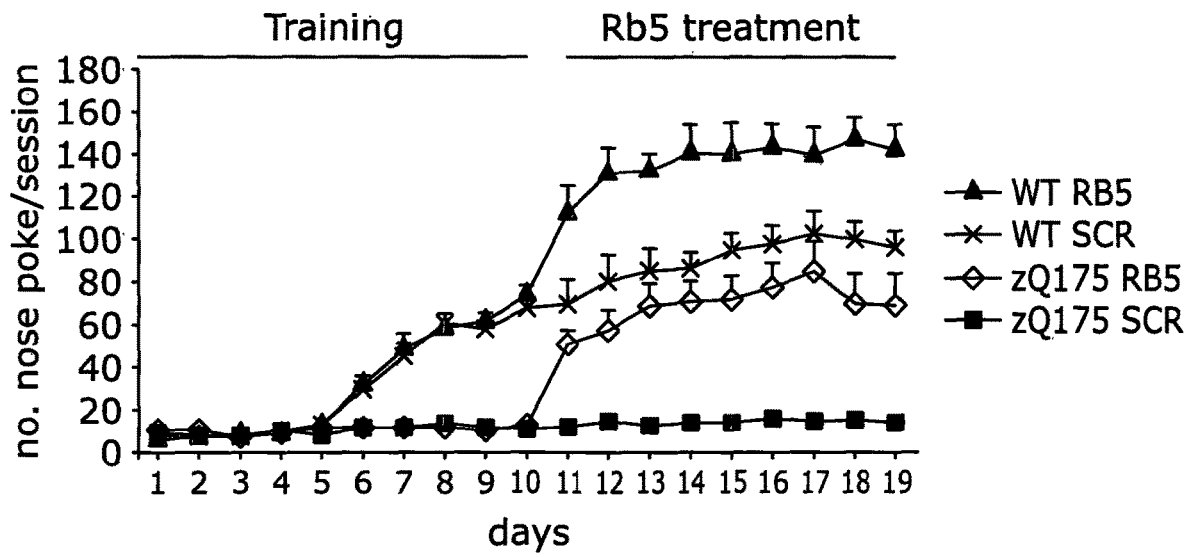
Figure 11:
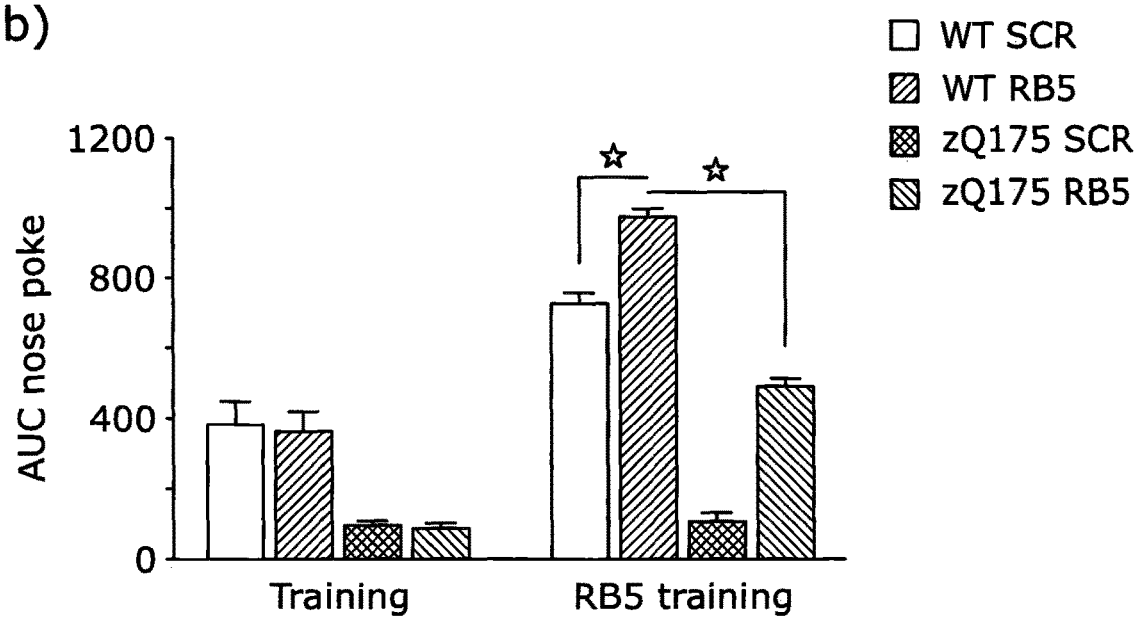

FIG. 11. RB5 improves cognitive performances in the zQ175 mouse model of Huntington's Disease.

WT and zQ175 mice underwent daily 20 minutes nose poke training for 10 consecutive days (days 1-10) on a simple fixed ratio (FR1) schedule of reinforcement. Starting from day 11 mice received one administration of RB5 (20 mg/kg. i.p.) 1 h before the nose poke training. RB5 significantly improved the nose poke responding of zQ175 female mice (Two-way interactions between genotype×gender $F_{1,57}$=4.383 P=0.041 and treatment×gender $F_{1,57}$=28.120 P<0.0001 were significant). Mean nose poke score was higher in female zQ175 than male zQ175, with a mean difference of 21.893 P=0.001. a) RB5 treatment improved performances of both WT and zQ175 female mice (two way ANOVA, time×treatment interaction $F_{18,648}$=23.314, P<0.001) with higher scores in female WT than female zQ175 (mean difference of 46.175 P=0.001). b) Analysis of area under curve (AUC) of nose pokes measured during training (Welch ANOVA, Games-Howell's post hoc, zQ175 vs WT P<0.05) and during RB5 treatment (Welch ANOVA, Games-Howell's post hoc, P<0.0001). Results show mean±s.e.m. White star P<0.0001.

DETAILED DESCRIPTION

Methods and Materials

Preparation of Peptides

Cell penetrating peptides against the ERK pathway as well as the scrambled control (ineffective) are custom synthesized by GENECUST EUROPE (Luxembourg). The sequences of the tested peptide (CPP-RB5) and its scrambled version (CPP-SCR) are:

```
CPP-RB5:
                                 (SEQ ID NO: 18)
GRKKRRQRRRPPQGGGGGEPRRTEGVGPGVPGEVEMVKGQPFDV

CPP-SCR:
                                 (SEQ ID NO: 19)
GRKKRRQRRRPPRVGPGVPEGVGVAVFGVKEPGQTGDVGPVGE
```

For all in vitro and in vivo experiments, batches of 200 mg, highly purified by high-performance liquid chromatography (HPLC) (≥95%) with C-terminal amino acid (last) in D form and acetylated N-Terminal (first) amino acid were used. For in vivo experiments the peptides were dissolved in PBS 1× and injected at indicated doses.

Pharmacological Treatments

L-Glutamic acid (G-6904, Sigma Aldrich) was dissolved in sterile water and used at final concentration of 100 µM during 10 min of stimulation.

3-nitropropionic acid (3-NP, N5636, Sigma, St. Louis, Mo.) was dissolved in distilled water to a concentration of 50 mg/ml and pH adjusted to 7.4 and passed through a 0.2-µm filter and kept at −80° C. until use.

Animals

C57BL/6 mice purchased from Charles River Laboratories were used as a source of primary striatal cultures and ex-vivo acute slices to perform both immunoblots and immunofluorescence. Mice were also subjected to behavioral and immunohistochemical investigations upon co-treatment with 3-NP and peptides.

CD1 mice purchased from Charles River Laboratories were used for testing the acute effect of CPP-RB5 and CPP-SCR and Object Recognition Test followed by immunofluorescence and IHC analysis.

HdhQ111 heterozygous mice (Jax®, Bar Harbour, Me., U.S.A.), zQ175 knock-in heterozygous (mix sex) carrying between 180 and 195 CAG repeats (CHDI-81003003, Psychogenics, Inc. Tarrytown, N.Y.) and Tg2576 transgenic male mice (C57BL6 and SLJ mix background, Taconic Biosciences) were used for IHC, IF and behavioural test.

ERK1 male KO and littermate controls, were generated as described previously and were used for ex vivo analysis.

Lister Hooded rats were purchased from Harlan Laboratories and used for Contextual Fear Conditioning Test.

Ex-Vivo System on Acute Brain Slices

Adult mice were anesthetized and decapitated. The brains were rapidly removed from the skull and put on a cool glass plate filled with ice-cold sucrose-based dissecting solution (87 mM NaCl, 2.5 mM KCl, 7 mM $MgCl_2$, 1 mM $NaH_2PO_4$, 75 mM sucrose, 25 mM $NaHCO_3$, 10 mM D-glucose, 0.5 mM $CaCl_2$), 2 mM kynurenic acid) and oxygenated with 95% $O_2$ and 5% CO2 and subsequently mounted on the vibratome stage (Vibratome, VT1000S-Leica Microsystems). 200 µm-thick slices were cut and transferred into the brain slice chamber (Brain slice chamber-BSC1—Scientific System design Inc., Mississauga, ON, Canada) and allowed to recover for 1 h at 32° C., with a constant perfusion of carboxygenated artificial cerebrospinal fluid (ACSF) in the presence of the Scramble or RB5 peptide (50 µM). Brain slice stimulation was performed with 100 µM glutamate in the chamber for 10 min. After rapid fixation in 4% PFA for 15 min at room temperature, slices were rinsed and the cryoprotected overnight at 4° C. in sucrose solution. On the following day slices were further cut in thinner slices of 18 µm using cryostat (Leica CM1850) and collected onto SuperFrost Plus slides (Thermo Scientific).

In Vivo Administration of Drugs

At the indicated times after drug treatments, animals were anaesthetised and transcardially perfused with ice-cold buffered 4% PFA. Brains were extracted, post-fixed overnight and transferred to 30% buffered sucrose for 24 h. Coronal sections were cut to a 35 µm thickness on a freezing microtome and stored in a cryoprotective solution at −20° C. until processing for immunohistochemistry or immunofluorescence.

Liquid Chromatography and Tandem Mass Spectrometry (HPLC-MS/MS)

Bioavailability of RB5 in the mouse brain was determined at different time intervals (1, 3, 6, 12 h) after a single i.p. administration of 20 mg/kg. RB5 was then quantified in mouse brain using HPLC-MS/MS. Brain samples were homogenized with 1:4 w/v of 50% acetonitrile, 5% TFA in water with an homogenizer ultra-turrax and then centrifuged at 13000 rpm for 10 min at 4° C. The supernatant was collected and centrifuged at 13000 rpm for 2 minutes at 4° C. The supernatant was then collected in ice, extracted using Sep-Pak cartridges C18, lyophilised and kept at 4° C. before HPLC-MS/MS analysis. Immediately before the analysis samples were suspended in 100 µL of 0.1% HCOOH in water/8% acetonitrile in auto-sampler vials.

HPLC-MS/MS analysis was performed using a system consisting of an Agilent 1200 series HPLC system coupled with an Agilent 6410 Triple Quadruple mass spectrometer. Mass Hunter Workstation v. B.01.03 software was used for data collection and processing (Agilent Technologies, Santa Clara, Calif., US). The quantification of mouse brain levels of RB5 and scramble peptides was carried out using an internal standard curve with peptide concentrations ranging from 0.1 to 4 ng per µl. RB5 and scramble peptides and the internal standard were separated at room temperature by injecting 10 µL of extracted sample onto a Jupiter C4 300 A analytical column, 2×150 mm, 5 µm particle size (Phenomenex, CA). Gradient elution was used for chromatographic separation, using 0.1% formic acid in water as solvent A, and acetonitrile as solvent B at a flow rate of 200 µl/min. The elution started with 92% of eluent A and 8% of eluent B maintained for 1 min, followed by a 4 min linear gradient to 75% of eluent B, a 1 min linear gradient to 99% of eluent B, a 2 min isocratic elution and a 0.5 min linear gradient to 8% of eluent B, which was maintained for 9.5 min to equilibrate the column. The samples were maintained at 4° C. in the autosampler.

Peptides were then detected on an Agilent 6410 QQQ mass spectrometer using the following parameters: positive ion mode, 5 kV capillary voltage, cone voltage 500 V, gas flow rate 8 L/min at 350° C., nebulizer gas pressure 40 PSI at 350° C., well time 75 msec and Q1 and Q3 set to unit resolution.

Immunofluorescence

Slides were placed in a humid chamber and 1 h after blocking in 5% normal goat serum and 0.1% Triton X-100 solution, they were incubated overnight at 4° C. with one of the following primary antibodies: anti-phospho-S6 ribosomal protein (Ser235/236) (1:200 Cell Signalling Technology, Danvers, Mass.), anti-phospho-S6 ribosomal protein (Ser240/244) (1:200 Cell Signalling Technology, Danvers, Mass.), anti-phospho (Ser10)-acetylated (Lys14) histone H3 (1:1000 Millipore, Billerica, Mass.) or Cleaved Caspase 3 (1:200 Cell Signalling Technology, Danvers, Mass.) and anti-NeuN (1:1000 Millipore, Billerica, Mass.) followed by appropriate secondary antibodies. Single and double-labelled images were obtained using a laser scanning confocal microscopy (Leica SP2) equipped with the corresponding lasers and the appropriate filters sets to avoid the cross-talk between the fluorochromes. Cells were sampled throughout the dorsal regions of the striatum with a 40× objective. Neuronal quantification is performed with ImageJ software by counting phospho-S6 immunoreactive or pH3 neurons among NeuN positive neurons in each slide (n=10 for each experimental group). The ratio of phospho-S6 or phospho-H3 positive cells between total NeuN positive neurons gave the percentage of phospho-S6 or phospho-H3 positive neurons for each field acquired (n=4) through the slide. Comparisons between groups of different treatments were performed using two-way ANOVA and post-hoc analysis with Bonferroni Test, in GraphPad Prism 5 software.

Western Blotting

Mice were sacrificed by decapitation and brain slices were freshly prepared according to the above ex-vivo system protocol and incubated in a perfusing chamber with the peptides. After stimulation with glutamate or saline, slices were then homogenised and used for protein determination using a DC Protein Assay kit (Bio-rad). Equal amounts of protein (5 or 10 µg, depending on the target protein) for each sample were loaded onto 12% polyacrylamide gels. Proteins were separated onto SDS/PAGE and transferred to nitrocellulose membranes. After incubation for 1 hr in blocking solution (TBS1λ, 0.1% Tween), membranes were incubated overnight with anti ERK2 (K-23):sc-153 (1:1000 Santa Cruz Biotechnology, Dallas, Tex.), phospho-p42-44 Map Kinase (Thr202/Tyr24) (1:1000 Cell Signalling Technology, Danvers, Mass.) and anti-GAPDH (FL-335): sc-25778 (1:1000 Santa Cruz Biotechnology, Dallas, Tex.). The immunoblots were analysed with ImageJ software to measure the optical density of the bands. The levels of each protein were normalized on the GAPDH loading control.

Neuronal Embryonic Cultures

Embryonic cultures (E16) were prepared from striata of WT mice, plated onto poly-L-lysine coated glass and kept for 10 days in culture medium as previously described (Fasano et al, Biol Psy 2009). Two different concentrations (20 µM and 50 µM) of CPP-RB5 and CPP-SCR peptides were added to the culture medium by the third day and replaced every day. On day 11, cells were fixed with 4% PFA pH 7.4 in PBS for 10 min.

Immunohistochemistry 1 h after CPP-RB5/CPP-SCR (20 mg/kg, i.p.) mice were anaesthetized and perfused via intracardiac infusion of ice-cold 4% PFA. Brains were rapidly extracted, post-fixed overnight and transferred to 25% buffered sucrose for 24 h. Coronal sections were cut at 30 µm thickness on a freezing microtome and stored in a cryoprotective solution at −20° C. until they were processed for immunohistochemistry. Free-floating sections were incubated with primary antibodies against anti-phospho-p44/42 MAP kinase (Thr202/Tyr204), anti-phospho-Elk-1 (Ser383), anti-phospho-Kv4.2 (Thr607)-R, anti-phospho-MSK-1, anti-phospho-MEK-1, c-Fos and Tyrosine Hydroxylase overnight at 4° C. Sections were then incubated with biotinylated goat anti-rabbit IgG (1:200, Vector Labs) for 2 h. Detection of the bound antibodies was carried out using a standard peroxidase-based method (ABC-kit, Vectastain, Vector Labs), followed by a DAB and $H_2O_2$ solution. Quantification of positive neurons were counted from striatum in 2-3 sections per mouse, bilaterally. Sample areas were visualized under a 20× objective in a Leica DM IRB microscope by a blind investigator to condition and counts per region were averaged across the sections using the ImageJ software.

TUNEL Staining

The DeadEnd Colorimetric TUNEL System (Promega) was used to detect apoptotic cells in cultured cells labelling the fragmented DNA of apoptotic cells using a modified TUNEL assay. TUNEL staining was realized with diaminobenzide (DAB) following the manufacture's protocol. Sample areas were digitized through a video camera (Nicon) connected to a Zeiss microscope using a 20× objective. 4 areas were counted and averaged for each plate.

3-Nitropropionic Acid Administrations In Vivo

Before use, CCP-SCR and CPP-RB5 were diluted in PBS 1× and injected twice a day at 12 hr intervals (20 mg/kg). 3-NP was injected 1 h after peptides once a day for 7 consecutive days (50 mg/kg) in male C57B/6 mice. All drugs were administered by intraperitoneal (i.p.) injection in a volume of 10 ml/kg. The mice were euthanized 1 hr after the last peptide injection and transcardially perfused with buffered 4% PFA, and processed for immunohistochemistry.

The DeadEnd Colorimetric TUNEL System (Promega) was used to detect apoptotic cells on tissue sections 35 mm thick. For each animal three consecutive coronal sections were taken, mounted on glass slides and processed for immunohistochemical analysis according to the recommended procedures. For quantification, the number of positive neurons in each section was counted across the dorsolateral region of the striatum of both hemispheres and means values were calculated.

Object Recognition Task (NOR)

The test was performed in an open square box (45×45×45 cm), placed in a quiet room with dim light. The objects used were: parallelepipeds in metal and glass vials filled with water. They had no natural significance for mice and they had never been associated with reinforcement before. The protocol required three days and it was performed as follows:

First day: the mice were individually placed in the empty arena for 5 min in order to familiarize with it and to measure their anxiety (thigmotaxis trial). The percentage of thigmotaxis is calculated as the time spent in the peripheral zone out of the total time spent in the arena (300 sec.). Animals showing a thigmotaxis>90% are discarded from the sample because considered biased for anxiety.

Second day: Mice were injected with either 20 mg/ml CPP-SCR or CPP-RB5 1 h prior to training and then they were placed into the arena for 10 minutes, where they were allowed to explore two identical objects (training trial). Therefore, two different measures (in seconds) for Left Object and Right Object were obtained. Successful trainings were considered those with a total object exploration of at least 8 seconds in 10 min; if an animal failed to reach this threshold, it was excluded from the experiment. Then, percentages of exploration for each object were calculated as: the time spent exploring LO or RO, out of the total time of exploration (RO+LO). According to these percentages, experimenter decided where to place the novel object for the test trial.

Third day: one of the two identical objects (Parallelepiped) was changed with a new object (Vial) and the mice were allowed to explore them for 10 minutes (test trial).

Times of exploration for the familiar object (FO) and for the novel object (NO) were separately recorded, with the same procedure as for the training trial. A cut-off of 6 seconds was also considered. In order to attest recognition memory, a discrimination index (D.I.) was calculated as (total time of exploration of NO−total time of exploration of FO)/total time of exploration of (FO+NO). D.I. index is comprised between −1 and +1. A D.I. of 1 would mean perfect memory retention for the FO. Conversely, the more time the animal spends exploring FO the lower will be the D.I. value, meaning poor memory retention for FO. SMART software (Panlab, Barcelona, Spain) was used to run the experiment.

Surgery and Microinfusions into the Dorsal Hippocampus

The subjects were adult male Lister hooded rats weighing 280-350 g. They were housed in pairs, in holding rooms maintained at 21° C. on a reversed-light cycle (12 h light/dark; lights on at 10:00 P.M.). All experiments were conducted in the dark period of the rats. Food and water were freely available throughout the experiment. Steel double guide cannulae aimed at the dorsal hippocampus (AP−3.50, relative to bregma) were surgical implanted under anaesthesia at least one week prior to behavioural training and microinfusions. Bilateral infusions with either 2 mg/ml CPP-SCR or CPP-RB5, 20 min prior to conditioning (pH 7.0, 1.0 ml/side, rate=0.5 ml/min) via the chronically indwelling cannula were carried out in awake rats using a syringe pump, connected to injectors (28 gauge, projecting 1 mm beyond the guide cannulae) by polyethylene tubing.

Contextual Fear Conditioning

Conditioning was performed in one of two distinct contexts. These contexts were designed to differ in a number of distinctive characteristics including size, spatial location, odour and lighting.

Rat protocol: during the 3 min conditioning training trial, rats received a single scrambled footshock (0.5 mA for 2 s) 2 min after being placed into one of the conditioning contexts (CtxA). All rats were returned to the home cages after conditioning. Retrieval tests 3 hr (post-retrieval short-term memory, STM), or 2 days (long-term memory, LTM) after recall again consisted of exposing the rat to the conditioning context for 2 min.

Mice protocol: after 120 sec of exploration, mice received 5 foot shocks (0.7 mA, 2-s duration, separated by 60-s intervals) delivered through the grid floor. Context Fear Memory was assessed 24 h later by returning mice for 5 min to the conditioning chamber and not delivering a foot shock.

For all protocols, freezing behavior served as a measure of conditioned fear to the context during the conditioning and retrieval tests of the behavioural procedures. This was video-recorded and quantified by an observer blind to the experimental group. One unit of freezing was defined as a continuous absence of movement other than that required for respiration in 1 s sampled every 10 s.

9-Hole Operant Boxes

Operant testing was conducted in 16 9-hole operant boxes. Each operant box contains a horizontal array of nine holes with infrared beams localised to the front of each hole to detect nose pokes. A peristaltic pump delivers liquid reinforcement (strawberry milk) into a magazine at the front of the box.

A week before starting the training, mice undergo water restriction for 18 hours/day and are kept under this regimen throughout the experimental procedures. Mice are taught to nose poke on a simple fixed ratio (FR1) schedule of reinforcement: to obtain reward, mice are required to respond to a stimulus light in the central hole via a single nose poke. Mice are trained daily on this program during 20 minutes sessions for 10 days (training phase). Once trained, animals were subdivided in 4 groups and injected with RB5 or scramble (10 mg/kg, i.p.) peptides 1 hour before being tested on FR1 schedule for other 9 days.

Results

A small polypeptide was designed over the unique N-terminal portion of ERK1 MAP kinase. This polypeptide, when attached to the kinase ERK1, confers an inhibitory effect on global ERK dependent signalling by significantly reducing the ability of ERK1 and ERK2 to shuttle from/to the nucleus, most likely by binding to components of the nuclear envelope. Importantly, the peptide sequence appears to be a functional domain since when removed from ERK1, this kinase behaves like ERK2 and, on the contrary, when attached to ERK2, this kinase starts behaving like ERK1.

However, such isolated peptide displays the unexpected pharmacological property to act as a MAPK3/ERK1 inhibitor, as detailed below, when expressed without being attached to ERK1 and in particular when fused to a cell penetrating peptide sequence. In the present invention, it was found that this MAPK3/ERK1 inhibitor designed around the N-terminal portion of ERK1, in particular the peptide sequence of SEQ ID No. 1, more particularly the RB5 peptide sequence, when administered in cells or in vivo in living animals, causes an enhancement of global ERK signalling in the nucleus, by facilitating nuclear translocation of ERK2, the major ERK isoform.

Enhancement of ERK Activity Through RB5 Peptide

In order to study biochemically the function of RB5 peptide on ERK activity, we used a recently established ex vivo system, in which brain slices can be freshly prepared from adult mice, incubated in a perfusing chamber with the peptides and stimulated with appropriate agonist and antagonists. As shown in FIG. 1a, brain slices previously incubated for 1 h with 50 µM CPP-RB5 or CPP-SCR peptides have been challenged with 100 µM glutamate and analyzed in Western blot. Phospho-ERK1 was equally increased in CPP-SCR and CPP-RB5 pre-treated slices while phosphorylation of ERK2 is selectively enhanced only in CPP-RB5 pre-treated slices indicating that this cell penetrating peptide is very effective in promoting ERK2 mediated signalling. Interestingly, no changes in the basal level of ERK1 and ERK2 proteins were detected.

Moreover, with this ex vivo system, induction of ERK signalling was monitored at the single cell level using phospho-specific antibodies against either histone H3 phosphorylation (pH3) or ribosomal protein S6 (pS6). RB5 promotes ERK-dependent nuclear signalling (ERK1/2 translocation and induction of histone H3 phosphorylation) in response to glutamate application (FIG. 1b, left panel). At the same time, cytoplasmic signalling is not activated (as measured by ribosomal S6 phosphorylation) (FIG. 1b, right panel). This phenotype equals what found in ERK1 KO cells, suggesting that RB5 is a pharmacological model in which ERK1 activity is attenuated and therefore ERK2 can be potentiated (FIG. 1c).

Based on these results, we examined the main involvement of RB5 in the nuclear signalling with in vivo experiments. Mice pre-treated with a single dose of CPP-RB5 or CPP-SCR (20 mg/kg) were perfused 1 h later and brain slices were processed for nuclear and cytoplasmic markers. As shown in FIG. 1, ERK induction was found significantly enhanced (panel d) as well as ERK-dependent nuclear signalling. Indeed, nuclear molecules as p-MSK-1, p-AcH3, p-ELK-1, c-Fos were found significantly increased upon CPP-RB5 administration (panels e-h). On the contrary, cytoplasmic signalling measured by ribosomal S6 phosphorylation was found at a lesser extent reduced in CPP-RB5 treated mice, while phosphorylation of voltage-gated potassium channel (pKv4.2) and MEK-1 was comparable between the two treatments (panels i-l). Finally, as observed in slices, RB5 in vivo administration did not alter either pERK (panel m), pAcH3 (panel n) or pS6 (panel o) in ERK1 KO mice, confirming that RB5 target is ERK1/MAPK3.

Pharmacokinetic Properties of RB5 Peptide in the Brain

In FIG. 2 the ability of RB5 to enhance ERK signalling in vivo was assessed. Firstly, RB5 activity remained high up to 6 h after injection (panel a) but down to basal level at 12 h, leading to an estimated an half-life of 9 h. Secondly, the dose response curve at 1 hr after injection was determined and confirmed that both 20 and 10 mg/kg (i.p.) doses are able to elevate pERK (panel b). Thirdly, we measured RB5 brain levels with mass spectrometry at different hours after a single i.p. administration of 20 mg/kg. High levels of RB5 were detected up to 6 h (panel c).

Decrease of Neuronal Death in Primary Striatal Culture Mediated by RB5 Peptide

To assay the effect of RB5 on neuronal survival, we prepared primary neuronal cultures from embryonic striata. Cells were exposed to CPP-SCR or CPP-RB5 peptides containing medium at two final concentrations of 20 µM or 50 µM for 7 consecutive days.

The DeadEnd Colorimetric TUNEL System was applied 24 h later to assay apoptotic cell death by measuring nuclear DNA fragmentation. As shown in FIG. 3, CPP-RB5 at higher concentration (50 µM) reduced apoptosis by 32% compared to CPP-SCR values.

Prevention of Cell Death in a Pharmacological Mouse Model of Huntington's Disease After having verified the effective capacity of RB5 peptide to enhance ERK activity in vitro and in the ex-vivo acute slice system, we tested the neuroprotective efficacy in vivo, in a pharmacological mouse model of Huntington's Disease. It is well known that 3-nitropropionic-acid (3-NP) selectively forms striatal lesions similar to those found in Huntington's Disease.

We set up a protocol in which male C57BL/6 mice were injected with CPP-SCR or CPP-RB5 peptides (20 mg/kg, i.p.) twice a day (every 12 h) for 7 days and 1 h after peptides injection they received one injection of 3-NP (50 mg/kg). At the end of treatment, animals were perfused and brains were prepared as for immunohistochemistry. As shown in FIG. 4, CPP-RB5 was able to prevent 3-NP-induced cell death in vivo, reducing apoptosis to control levels (panels a-b) and reduce pre-apoptotic levels of Caspase 3 marker to control levels (panels c-d).

Prevention of Cell Death in a Genetic Mouse Model of Huntington's Disease

We also evaluated the potential neuroprotective effect of RB5, in hdhQ111 transgenic mice, a late onset genetic model of Huntington's Disease. hdhQ111 mice were treated (20 mg/kg, i.p., twice a day) for 7 days (FIG. 5). It was found that RB5 not only elevated pERK in WT and mutant striata (panel a,b) but also prevents degeneration in the hdhQ111 mutants (panel c-f).

Prevention of Cell Death in a Pharmacological Mouse Model of Parkinson's Disease We have assessed the neuroprotective effect of RB5 in the MPTP (1-methyl-4-phenyl-1,2,3,6-tetrahydropyridine) neurotoxin model of Parkinson's Disease (FIG. 6). Mice have been treated with MPTP or vehicle (20 mg/kg, i.p) for 4 days. RB5 or scramble peptide (20 mg/kg, i.p) was injected 1 h before MPTP/vehicle. Neurodegeneration was prevented, as assessed by tyrosine hydroxylase (TH) staining (panel a, b), TUNEL (panel c, d) and cleaved caspase 3 (panel e, f), confirming a strong neuroprotective effect.

Prevention of Cell Death in a Genetic Mouse Model (Tg2576) of Alzheimer's Disease The genetic model of Alzheimer's Disease Tg2576 and their WT controls have been treated for 7 days with RB5/scramble peptide (20 mg/kg, i.p). A shown in FIG. 7, RB5 increased pERK in the Tg2576 mutants (panel a-d) and at the same time reduced the levels of cleaved caspase-3 staining (panel e-f), confirming a strong neuroprotective effect.

Enhancement of Memory Consolidation in Object Recognition Test

RB5 peptide is thought to up-regulate ERK signalling in neurons. This would lead to an enhanced activation of the pathway and thus to an augmented protein synthesis. Since gene transcription is the biological mechanism underlying memory consolidation, a memory improvement is the expected behavioral result. Therefore, we performed the Object Recognition Task (ORT), a test commonly used to study explicit memory in rodents.

There are different variants of this test and the one's chosen allows investigating the memory for unique events, namely the one-trial object recognition test in which a delayed discrimination between a novel and a familiar object is requested. 1 h before the beginning of the test mice underwent intraperitoneal injection of CPP-SCR or CPP-RB5 peptides and then they were examined after different time points (24, 48, 72 and 120 h). As shown in FIG. 8, CPP-RB5 treated mice had greater performances in remembering the object both at 24, 48, 72 and surprisingly 120 h later when compared to their CPP-SCR animals (panel a). Lastly, at 168 h, the performance of RB5 group dropped to basal levels indistinguishable from SCR group (panel b). This means that RB5 did improve memory consolidation of the mice allowing them to spend more time with the new object on memory test day.

Improvement of Emotional Memory Formation in CFC

We also tested the effect of RB5 on the acquisition and the expression of the contextual fear conditioning (CFC) in which rodents learn to associate an innocuous conditioned stimulus (CS) such as a context with a noxious unconditioned stimulus (US) such as a footshock. CFC has widely been used as a behavioral paradigm to evaluate associative learning and memory functions. Awake rats were infused bilaterally into the hippocampus with either 2 mg/ml CPP-SCR or CPP-RB5 20 min prior to conditioning in the chamber box (context). Short-term memory (STM) and long-term memory (LTM) were assessed by measuring freezing behavior during a test performed 3 h and 2 days after training. As shown in FIG. 9, CPP-RB5 infusion into the dorsal hippocampus prior to CFC enhanced the acquisition of contextual fear memory and resulted in a stronger long-term fear memory.

Prevention of Memory Loss in a Mouse Model (Tg2576) of Alzheimer's Disease

Moreover, we investigated whether enhancement of ERK activity through RB5 peptide was able to modulate cognitive impairment in Alzheimer disease. A transgenic model of AD (Tg2576-APPswe mice) was used during the late symptomatic phase to test the possibility of halting cognitive impairment. Aged Tg2576 and WT mice were treated with either CPP-SCR or CPP-RB5 (20 mg/kg, i.p.) before Contextual Fear Conditioning (CFC) training and tested for memory retention 24 h later. As shown in FIG. 10, CPP-RB5 peptide rescued already present memory impairments in aged Tg2576 mice back to WT levels.

Enhancement of Cognitive Performances in the zQ175 Mouse Model of Huntington's Disease.

We also evaluated the effect of RB5 on the acquisition of a procedural learning task such as 'nose poking' in a model of HD with early onset of cognitive deficits, the zQ175 transgenic mice. The nose poke training was conducted in 9-hole operant boxes. In this task mice were required to respond to a stimulus light in the central hole via a single nose poke to obtain a liquid reward. After 10 days of training zQ175 mice showed a clear impairment in learning this task. However, upon RB5 administration all animals significantly changed their performances over time with a clear sex difference (FIG. 11a-b). In particular, both wild type (WT) and zQ175 female mice showed a significant enhancement of the responses over 9 days of RB5 treatment.

Altogether, this evidence supports the use of RB5 and derivatives or homologues as an effective neuroprotective and cognitive enhancing treatment for patients affected by neurodegenerative disorders and for improving cognition in normal individuals.

CONCLUSION

We have shown that short peptides derived from the N-Terminal of ERK1 MAP kinase (both human and mouse)

can prevent neuronal apoptosis in vitro and in vivo. The peptides of the invention have the ability to specifically stimulate nuclear translocation of ERK and thus stimulate ERK-mediated gene transcription and chromatin remodelling in the brain. Brain delivery of the peptides is advantageously achieved through specific tagging with cell penetrating peptide sequences. Then the peptides can pass through the blood brain barrier and through plasma membranes of neuronal cells. Such peptides act as neuroprotective agents which could be useful for the treatment of a number of neurodegenerative diseases or disorders. Further, the peptides of the invention display positive effects on both neuronal cell survival and cognition and represent a therapy for a number of major fatal brain disorders currently without effective treatment, both improving cognitive deficits and blocking neurodegeneration. Moreover, the peptides of the invention improve cognition also in the absence of neurodegeneration and so they are suitable for cognitive enhancement in healthy individuals.

The invention claimed is:

1. A neuroprotective peptide for inhibiting Mitogen-activated protein kinase 3 (MAPK3) protein kinase signaling, consisting of an amino acid sequence:
   i) QGGGGGEPRRTEGVGPGVPGEVEMVKGQPFDV (SEQ ID NO:1) hereafter named RB5; or
   ii) a sequence sharing at least 96% identity with peptide i).

2. A pharmaceutical composition comprising:
   the neuroprotective peptide according to claim 1; and
   a pharmaceutically acceptable carrier, adjuvant, diluent or excipient.

3. A nucleic acid molecule encoding the neuroprotective peptide according to claim 1.

4. A combination therapeutic, comprising:
   the neuroprotective peptide according to claim 1; or
   a nucleic acid molecule encoding the neuroprotective peptide; or
   a pharmaceutical composition comprising the neuroprotective peptide or the nucleic acid molecule; and
   at least one other therapeutic for enhancing cognitive ability of the brain.

5. A pharmaceutical composition comprising:
   a nucleic acid molecule encoding the neuroprotective peptide according to claim 1; and
   a pharmaceutically acceptable carrier, adjuvant, diluent or excipient.

6. A neuroprotective peptide for inhibiting Mitogen-activated protein kinase 3 (MAPK3) protein kinase signaling wherein said neuroprotective peptide consists of the sequence (SEQ ID NO: 18)
GRKKRRQRRRPPQGGGGGEPRRTEGVGPGVPGEVEMVKGQPFDV.

7. A method for enhancing cognitive ability comprising administering to an individual needing or desiring said improved cognitive ability an effective amount of:
- the neuroprotective peptide according to claim 1; or
- a nucleic acid molecule encoding the neuroprotective peptide; or
- a pharmaceutical composition comprising the neuroprotective peptide or the nucleic acid molecule.

* * * * *

SEQUENCE LISTING

```
<160> NUMBER OF SEQ ID NOS: 19

<210> SEQ ID NO 1
<211> LENGTH: 32
<212> TYPE: PRT
<213> ORGANISM: Homo sapiens

<400> SEQUENCE: 1

Gln Gly Gly Gly Gly Gly Glu Pro Arg Thr Glu Gly Val Gly Pro
1               5                   10                  15

Gly Val Pro Gly Glu Val Glu Met Val Lys Gly Gln Pro Phe Asp Val
            20                  25                  30

<210> SEQ ID NO 2
<211> LENGTH: 10
<212> TYPE: PRT
<213> ORGANISM: Homo sapiens

<400> SEQUENCE: 2

Gly Arg Lys Lys Arg Arg Gln Arg Arg Arg
1               5                   10

<210> SEQ ID NO 3
<211> LENGTH: 16
<212> TYPE: PRT
<213> ORGANISM: Homo sapiens

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 7
<212> TYPE: PRT
<213> ORGANISM: Homo sapiens

<400> SEQUENCE: 4

Arg Arg Arg Arg Arg Arg Arg
1               5

<210> SEQ ID NO 5
<211> LENGTH: 9
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 5

Xaa Arg Arg Arg Arg Arg Arg Arg Xaa
```

```
<210> SEQ ID NO 6
<211> LENGTH: 9
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 6

Xaa Arg Arg Arg Xaa Arg Arg Arg Arg
1               5

<210> SEQ ID NO 7
<211> LENGTH: 9
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 7

Arg Arg Arg Xaa Arg Arg Arg Arg Xaa
1               5

<210> SEQ ID NO 8
<211> LENGTH: 9
<212> TYPE: PRT
<213> ORGANISM: Homo sapiens
<220> FEATURE:
<221> NAME/KEY: misc_feature
<222> LOCATION: (8)..(9)
<223> OTHER INFORMATION: Xaa can be any naturally occurring amino acid

<400> SEQUENCE: 8

Arg Arg Arg Arg Arg Arg Arg Xaa Xaa
1               5

<210> SEQ ID NO 9
<211> LENGTH: 9
<212> TYPE: PRT
<213> ORGANISM: Homo sapiens
<220> FEATURE:
<221> NAME/KEY: misc_feature
<222> LOCATION: (1)..(2)
<223> OTHER INFORMATION: Xaa can be any naturally occurring amino acid

<400> SEQUENCE: 9

Xaa Xaa Arg Arg Arg Arg Arg Arg Arg
1               5

<210> SEQ ID NO 10
<211> LENGTH: 11
<212> TYPE: PRT
<213> ORGANISM: Homo sapiens

<400> SEQUENCE: 10

Arg Arg Arg Arg Arg Arg Arg Arg Arg Arg Arg
```

```
1               5                   10
```

<210> SEQ ID NO 11
<211> LENGTH: 13
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 11

```
Xaa Arg Arg Arg Arg Arg Xaa Arg Arg Arg Arg Arg Arg
1               5                   10
```

<210> SEQ ID NO 12
<211> LENGTH: 14
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 12

```
Arg Arg Arg Arg Arg Xaa Arg Arg Arg Arg Arg Arg Arg Xaa
1               5                   10
```

<210> SEQ ID NO 13
<211> LENGTH: 22
<212> TYPE: PRT
<213> ORGANISM: Homo sapiens

<400> SEQUENCE: 13

```
Gly Ala Tyr Asp Leu Arg Arg Arg Glu Arg Gln Ser Arg Leu Arg Arg
1               5                   10                  15

Arg Glu Arg Gln Ser Arg
            20
```

<210> SEQ ID NO 14
<211> LENGTH: 14
<212> TYPE: PRT
<213> ORGANISM: Homo sapiens

<400> SEQUENCE: 14

```
Ser Arg Arg Ala Arg Arg Ser Pro Arg His Leu Gly Ser Gly
1               5                   10
```

<210> SEQ ID NO 15
<211> LENGTH: 16
<212> TYPE: PRT
<213> ORGANISM: Homo sapiens

<400> SEQUENCE: 15

```
Leu Arg Arg Glu Arg Gln Ser Arg Leu Arg Arg Glu Arg Gln Ser Arg
1               5                   10                  15
```

<210> SEQ ID NO 16
<211> LENGTH: 19

```
<212> TYPE: PRT
<213> ORGANISM: Homo sapiens

<400> SEQUENCE: 16

Val Lys Arg Gly Leu Lys Leu Arg His Val Arg Pro Arg Val Thr Arg
1               5                   10                  15

Met Asp Val

<210> SEQ ID NO 17
<211> LENGTH: 16
<212> TYPE: PRT
<213> ORGANISM: Homo sapiens

<400> SEQUENCE: 17

Arg Lys Lys Arg Arg Arg Glu Ser Arg Lys Lys Arg Arg Arg Glu Ser
1               5                   10                  15

<210> SEQ ID NO 18
<211> LENGTH: 44
<212> TYPE: PRT
<213> ORGANISM: Homo sapiens

<400> SEQUENCE: 18

Gly Arg Lys Lys Arg Arg Gln Arg Arg Pro Pro Gln Gly Gly Gly
1               5                   10                  15

Gly Gly Glu Pro Arg Arg Thr Glu Gly Val Gly Pro Gly Val Pro Gly
            20                  25                  30

Glu Val Glu Met Val Lys Gly Gln Pro Phe Asp Val
        35                  40

<210> SEQ ID NO 19
<211> LENGTH: 43
<212> TYPE: PRT
<213> ORGANISM: Homo sapiens

<400> SEQUENCE: 19

Gly Arg Lys Lys Arg Arg Gln Arg Arg Pro Pro Arg Val Gly Pro
1               5                   10                  15

Gly Val Pro Glu Gly Val Gly Val Ala Val Phe Gly Val Lys Glu Pro
            20                  25                  30

Gly Gln Thr Gly Asp Val Gly Pro Val Gly Glu
        35                  40
```